(12) United States Patent
Pangarkar et al.

(10) Patent No.: US 10,753,920 B1
(45) Date of Patent: Aug. 25, 2020

(54) DEVICES, SYSTEMS, AND METHODS FOR CELL ANALYSIS IN MICROGRAVITY

(71) Applicant: Theranos, Inc., Palo Alto, CA (US)

(72) Inventors: Chinmay Pangarkar, Palo Alto, CA (US); Elizabeth A. Holmes, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 734 days.

(21) Appl. No.: 14/309,689

(22) Filed: Jun. 19, 2014

Related U.S. Application Data

(60) Provisional application No. 61/837,151, filed on Jun. 19, 2013, provisional application No. 61/837,167, filed on Jun. 19, 2013.

(51) Int. Cl.
  *G01N 33/483* (2006.01)
  *G01N 15/00* (2006.01)

(52) U.S. Cl.
  CPC ....... *G01N 33/4833* (2013.01); *G01N 33/483* (2013.01); *G01N 2015/0065* (2013.01)

(58) Field of Classification Search
  CPC ............ G01N 33/4833; G01N 33/483; G01N 2015/0065
  See application file for complete search history.

(56) References Cited

U.S. PATENT DOCUMENTS

| | | | |
|---|---|---|---|
| 9,562,860 B1 | 2/2017 | Pangarkar et al. | |
| 2003/0104494 A1* | 6/2003 | Ravkin | B82Y 30/00 506/39 |
| 2008/0113358 A1* | 5/2008 | Kapur | G01N 33/689 435/6.12 |
| 2009/0081773 A1* | 3/2009 | Kaufman | G01N 1/2813 435/309.1 |

* cited by examiner

*Primary Examiner* — Gailene Gabel

(57) ABSTRACT

Devices, systems and methods for optical analysis of cells in microgravity are disclosed.
Effective cellular microscopic and image analysis requires placement of cells into a proper focal plane, region, or volume. Such placement often requires immobilization of the cells. Cell settling onto a substrate is often sufficient for cell immobilization; however, no significant settling occurs in microgravity. Cell immobilization in microgravity may be accomplished by treatment of a substrate, the cells, or both effective that the substrate captures and immobilizes the cells for inspection. Cells may be immobilized in microgravity by adhering magnetic particles to the cells and applying a magnetic field. Cells may be placed in a proper location for viewing in microgravity by placing the cells into a small chamber or narrow channel. Centrifugal force may effect cell settling and aid cell immobilization. Proper placement or immobilization of cells aids cellular microscopic and image analysis in microgravity.

11 Claims, 10 Drawing Sheets

DEVICES, SYSTEMS, AND METHODS FOR CELL ANALYSIS IN MICROGRAVITY

CROSS-REFERENCE TO RELATED APPLICATIONS

This application claims the benefit of, and priority under 35 U.S.C. § 119 to, U.S. Patent Application 61/837,151, filed Jun. 19, 2013 and U.S. Patent Application 61/837,167, filed Jun. 19, 2013, the entire contents of both of which applications are hereby incorporated by reference in their entireties.

BACKGROUND

Analysis of biological samples from a subject may be important for health-related diagnosing, monitoring and/or treating of the subject. A variety of methods are known for the analysis of biological samples.

In some instances, cells present in biological samples are examined, and their characteristics detected, classified, enumerated, identified, or otherwise investigated. For example, cells present in biological samples may be investigated by optical means, including by microscopic analysis, image analysis, and other optical means.

However, the collection of cells from biological samples, the aggregation of cells where desired, the treatment of cells, the imaging of these cells, and the analysis of resulting images and optical information present many problems. In addition, the collection and analysis of biological samples in microgravity (e.g., when the sample is analyzed when in free-fall, in orbit, in space en route to an extra-terrestrial destination, or otherwise subject to reduced gravity) adds additional difficulties to the analysis of biological samples.

Accordingly, in order to provide better diagnosing, monitoring, and/or treating of subjects, particularly in order to provide better devices, systems, and methods for analyzing biological samples in microgravity, improvements in the analysis of biological samples are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Devices, systems and methods for optical analysis of cells in microgravity are disclosed.

In microgravity, objects experience little or no gravitational force, and so do not fall in air, nor settle in liquids to any significant extent. For this reason, in orbit around the Earth or in other microgravity conditions, many actions expected of objects on Earth do not occur, or occur with much less force or speed. For example, under conditions of microgravity, cells and particles in liquids do not settle to the bottom of a channel or chamber containing them, and gas bubbles do not rise in liquids, Accordingly, in the absence of significant gravitational force, other forces or strategies must be used to cause cells and particles in a fluid to settle, or to cause and direct their motion within liquids.

Imaging of cells, particles, crystals, or other objects present in samples, such as fluid samples (e.g., blood, urine, or other fluid biological samples) is enhanced by positioning the cells, particles, crystals, or other objects in a single focal plane, or within a focal region or volume. (Hereinafter, the term "cells" will be understood to refer collectively to cells, particles, crystals, and other constituents of fluid biological samples.) However, in microgravity, cells will not settle onto a lower surface of a channel or chamber, and so will not significantly settle into such a focal plane, region, or volume. For this reason, steps must be taken to insure that cells in a fluid biological sample move to, and remain at, a desired location in an imaging apparatus.

Applicant discloses herein that cells in a fluid biological sample may be positioned in an imaging apparatus for imaging under microgravity conditions by: immobilizing the cells onto an imaging surface; moving cells under the influence of a magnetic field; constraining the cells within a small space so that the cells are in position for imaging; moving cells to an imaging surface by centrifugation; and combinations thereof. Methods, systems, and devices disclosed herein for positioning cells in fluid biological samples for imaging under microgravity may also be used under normal gravity conditions.

In embodiments, cells within a fluid biological sample may be immobilized onto a substrate (e.g., an inner surface of a transparent or translucent window or other optically suitable surface configured for imaging). In embodiments, cells may be immobilized by treatment of the substrate with material which adheres to the cells. In embodiments, cells within a fluid biological sample may be treated with material which adheres to the substrate. In embodiments, cells within a fluid biological sample may be treated with material which adheres to a substrate, where the substrate has been treated with material which adheres to the cells or to material with which the cells have been treated.

For example, an optically transmissive substrate may be coated (on a surface which contacts a fluid biological sample) with antibodies, polypeptides, lectins, polymers, glues, resins, lipids, polynucleotides or nucleic acid analogs, oligosaccharides or polysaccharides, cell receptors, immunoadhesins, ligands, biotin, avidin or streptavidin, or derivatives or combinations thereof. Such material coated onto an optically transmissive substrate may be termed an "adhesion agent" or "adhesion agents" and may be attached to the substrate by any suitable method, either covalently or non-covalently. Placing the fluid biological sample in contact with the coated optically transmissive substrate allows cells in the sample to contact the substrate; upon contact, the cells adhere to the substrate and remain attached to it. In embodiments, a fluid biological sample may flow into a channel or chamber in which at least one channel wall or chamber wall is, or includes, a coated optically transmissive substrate, where such flow is effective to contact cells with the substrate. In embodiments, imaging of cells in the fluid biological sample is performed while the cells are substantially immobile within the chamber. In embodiments, imaging of cells in the fluid biological sample is performed while the cells are substantially immobile within the chamber and attached to the substrate. In embodiments, such flow of a fluid biological sample comprises flow of a single stream of fluid within the chamber or channel. In embodiments, such flow of a fluid biological sample comprises flow of a single stream of fluid within the chamber or channel, without a fluid sheath, or other fluid flow for aligning or constraining cells to a particular region of the chamber or channel during fluid flow. In embodiments, such flow of a fluid biological sample comprises flow of a single stream of fluid within the chamber or channel, without a sheath fluid, or other additional fluid or stream for aligning or constraining cells to a particular region of the chamber or channel during fluid flow.

In embodiments, a substrate, or a chamber including a substrate such as an optically transmissive substrate, may be configured to provide laminar flow within the chamber or across the substrate. In embodiments, a substrate, or a chamber including a substrate such as an optically transmissive substrate, may be configured to provide turbulent flow within the chamber or across the substrate. In embodiments, a substrate, or a chamber including a substrate such as an optically transmissive substrate, may be configured so that flow across the substrate enhances the probability that a cell in the biological sample will likely contact the substrate multiple times. In embodiments, a fluid biological sample may be caused to flow past such a substrate multiple times (e.g., by multiple filling and flushing of the sample across the substrate). In embodiments, a fluid biological sample may be caused to flow past a substrate multiple times effective that cells in the sample have a high probability of contacting the substrate at least once during such flow. In embodiments, treatment of a substrate is effective to enhance cell immobilization on a substrate. Such immobilization of cells on a substrate is effective for imaging of the cells, and for improving imaging of cells as compared to cell imaging absent such immobilization.

In embodiments, treatment of cells may be performed, in addition to treatment of a substrate, and such combined treatments may be effective to enhance cell immobilization on a substrate. For example, cells in a fluid biological sample may be treated in order to provide means, or to enhance means, for attaching cells to a substrate. Thus, for example, cells in a fluid biological sample may be treated to provide them with, e.g., antibodies, polypeptides, lectins, polymers, glues, resins, lipids, polynucleotides or nucleic acid analogs, oligosaccharides or polysaccharides, cell receptors, immunoadhesins, ligands, biotin, avidin or streptavidin, or derivatives or combinations thereof. Such treatment of a fluid biological sample may be performed on a sample to be imaged in a cuvette or other imaging device that has been treated to enhance cell immobilization; in embodiments, such treatment of cells in a fluid biological sample alone may be effective for such immobilization, and may be performed on a sample to be imaged in a cuvette or other imaging device having an optically transmissive substrate that has not been treated to enhance cell immobilization.

Such immobilization of cells on a substrate by treatment of an inner surface of the substrate, or by treatment of the cells, or both, is effective for imaging of the cells. For example, where the substrate comprises an optically transmissive substrate, immobilization of the cells on an inner surface of the substrate allows imaging of the cells through the substrate by imaging apparatus placed on or near an outer (external) surface of the optically transmissive substrate.

Thus, in embodiments in which a fluid biological sample is placed in an imaging device having an optically transmissive substrate treated to immobilize cells on the substrate, the cells placed in optimal position for imaging. Such positioning of cells within such a chamber is effective for imaging of the cells, and for improving imaging of cells as compared to cell imaging absent such immobilization.

In further embodiments, cells may be moved under the influence of a magnetic field. In embodiments, cells may be immobilized on a substrate under the influence of a magnetic field. For example, cells may be immobilized in microgravity by adhering magnetic particles to the cells and applying a magnetic field. In embodiments, magnetic particles may be polystyrene or other polymer magnetic particles; agarose or other polysaccharide magnetic particles; metal or metal-containing compound magnetic particle; iron- or other metal-containing peptide magnetic particle; or any other suitable magnetic particle. Magnetic particles may be attached to cells, for example, by means of antibodies, lectins, nucleic acids, or any other agent which binds cells, attached to the magnetic particles. In embodiments, magnetic particles are provided or treated so they include agents that bind native cells in a fluid biological sample. In embodiments, cells in a fluid biological sample are treated to enhance the attachment of magnetic particles to them.

In embodiments where magnetic particles are attached to cells in a fluid biological sample, application of a magnetic field is effective to move cells in a desired direction (e.g., towards the source of the magnetic field) and to a desired location (e.g., to a desired imaging location, or imaging region, or imaging volume). In embodiments where magnetic particles are attached to cells in a fluid biological sample, cells may be immobilized on a substrate by application of a magnetic field. Such immobilization of cells on a substrate by application of a magnetic field is effective for imaging of the cells. For example, where the substrate comprises an optically transmissive substrate, immobilization of the cells on an inner surface of the substrate allows imaging of the cells through the substrate by imaging apparatus placed on or near an outer (external) surface of the optically transmissive substrate.

Thus, in embodiments in which a fluid biological sample is placed in an imaging device having an optically transmissive substrate configured for use with magnetic particles attached to cells, effective that cells may be positioned by application of a magnetic field to be near to, or in contact with, the substrate, the cells placed in optimal position for imaging. Such positioning of cells within such a chamber is effective for imaging of the cells, and for improving imaging of cells as compared to cell imaging absent such immobilization.

In further embodiments, cells may be placed in a proper location for imaging in microgravity by placing the cells within a small chamber or narrow channel. For example, a chamber for containing a fluid biological sample for imaging may have an optically transmissive surface suitable for use during imaging, which includes an optically transmissive substrate, may include a chamber portion adjacent the optically transmissive substrate with dimensions near to those of cells found in the biological sample. For example, an internal chamber may have a height substantially perpendicular to said optically transmissive surface, wherein said height is of a size similar to a cross-sectional dimension of a cell from said fluid biological sample, said height being configured to constrain a cell positioned within said chamber to a desired region within said channel. Cells located in such a chamber portion will, of necessity, be placed near to the optically transmissive substrate and so be placed in optimal position for imaging. In embodiments, such a chamber has a narrow cross-sectional area adjacent to the optically transmissive substrate that constrains a cell within a fluid biological sample to be near to, or in contact with, the substrate. In embodiments, such a chamber comprises an elongated chamber or an elongated channel having a length adjacent the optically transmissive substrate, where the elongated chamber or channel has a narrow cross-section area partly or entirely through the length of the elongated chamber that constrains a cell within a fluid biological sample to be near to, or in contact with, the substrate. In embodiments, such a chamber has a small volume, and a narrow cross-sectional area adjacent to the optically transmissive substrate that constrains a cell within a fluid biological sample to be near to, or in contact with, the substrate.

In embodiments, cells may be placed in a chamber, and the dimensions of the chamber, or a portion thereof, may be altered so as to provide a small chamber, a narrow chamber, or a chamber having a portion or region of small dimension effective to constrain cells within the chamber, or chamber region, to be disposed in a proper location for imaging in microgravity. For example, an imaging device may have an internal chamber having a height substantially perpendicular to said optically transmissive surface, wherein said height may be altered, e.g., while a fluid sample is held within the chamber. In a first configuration, such a height may be large as compared to a cross-sectional dimension of a cell from said fluid biological sample. In a second configuration, such a height may be of a size similar to a cross-sectional dimension of a cell from said fluid biological sample, said height in said second configuration being configured to constrain a cell positioned within said chamber to a desired region within said channel. Cells located in such a chamber portion in a second configuration will, of necessity, be placed near to the optically transmissive substrate and so be placed in optimal position for imaging. Accordingly, Applicant discloses an imaging device comprising a chamber for imaging cells, wherein the chamber may assume a configuration comprising a narrow chamber, or a chamber with a narrow region or portion, effective that cells within such a narrow chamber or chamber portion are close to, or in contact with, an optically transmissive surface effective for imaging the cells. Accordingly, Applicant discloses an imaging device comprising a chamber for imaging cells wherein the chamber has a first configuration and a second configuration, and the chamber configuration may be changed from said first configuration to said second configuration while containing a fluid sample containing cells, wherein the second configuration of the chamber comprises a narrow chamber, or chamber with a narrow region or portion, effective that cells within such a narrow chamber or chamber portion are close to, or in contact with, an optically transmissive surface effective for imaging the cells.

Thus, in embodiments in which a fluid biological sample is placed in an imaging device having an optically transmissive substrate adjacent a chamber that constrains a cell to be near to, or in contact with, the substrate, the cells are placed in optimal position for imaging. Such positioning of cells within such a chamber is effective for imaging of the cells, and for improving imaging of cells as compared to cell imaging absent such immobilization. In embodiments, the substrate may include adhesion agents, or be otherwise configured to bind or localize cells from the fluid biological sample, effective to aid in imaging such cells.

In further embodiments, cells may be placed in a proper location for imaging in microgravity by application of centrifugal force (by rotation, e.g., centrifugation). For example, an imaging device having a chamber for containing a fluid biological sample which includes an optically transmissive substrate may be rotated in an orientation such that cells will flow towards and onto the substrate. In embodiments, such a substrate may be treated with adhesion agents to attach cells to the substrate. In embodiments, such an imaging device may be configured for use with magnetic particles, and for use with a magnetic field. In embodiments, such an imaging device may have a chamber configured to constrain or to position cells near to the optically transmissive substrate. Application of centrifugal force to a fluid biological sample, or to an imaging device containing a fluid biological sample, may be performed with any imaging device or method disclosed herein. Such application of centrifugal force aids in positioning cells near to an optically transmissive substrate and so aids the positioning of cells in an optimal position for imaging.

Thus, in embodiments, centrifugal force may be used, alone or in conjunction with adhesion agents, or magnetic particles, or constraint within a chamber, or combinations thereof, to aid cell settling and aid cell immobilization on or near a substrate. Proper placement or immobilization of cells aids cellular microscopic and image analysis in microgravity.

Cells within a fluid biological sample may be immobilized by increasing the viscosity of the fluid, so that cells within the fluid sample may not move, or may only move slowly within the fluid. Immobilizing or reducing the speed of movement of cells within a fluid sample by increasing the viscosity of the fluid aids in imaging such cells. Such an increase in viscosity may be performed alone, in conjunction with, or following adhering cells to a surface, and may be performed alone, in conjunction with, or following movement of cells by use of a magnetic field, or of centrifugation, or of constraint within a narrow portion of a chamber. Increasing the viscosity of the fluid following adhesion of the cells to a surface (e.g., by use of an adhesion agent), or following application of a magnetic field (e.g., following application of a magnetic field effective to move cells attached to magnetic beads or magnetic particles), or following centrifugation, or following flow of at least a portion of the fluid sample into a narrow or constricted region of a cuvette (e.g., effective to constrain cells in the fluid to within small space effective to position the cells for imaging) is effective to maintain the cells in position during imaging. In embodiments, the viscosity of a fluid biological sample may be increased by mixing the sample with a suitable reagent (e.g., one including a fixative, or a cross-linking agent, or an enzyme, or one or more other components which may form a gel or matrix within the fluid), may be increased by altering the temperature of the fluid (e.g., heating or cooling), may be altered by illumination of the fluid (e.g., where a photosensitive component is found within or added to the fluid sample), or a combination thereof.

Imaging devices, systems containing such imaging devices, and methods of using the imaging devices disclosed herein are effective to provide imaging of cells in fluid biological samples in microgravity conditions. Prior devices, systems and methods are typically ineffective or unsuitable for use in microgravity conditions. Accordingly, the imaging devices, systems containing such imaging devices, and methods disclosed herein provide advantages over the art.

Imaging devices, and methods of using the imaging devices disclosed herein, may be useful as part of, and may be used with, automatic sample analysis devices and automatic sample analysis systems. Such automatic sample analysis devices and automatic sample analysis systems may be configured to analyze a biological sample, e.g., by detecting the presence of one or more target biological markers in a sample. Such automatic sample analysis devices and automatic sample analysis systems may be configured to analyze a biological sample, e.g., by detecting the presence of one or more target biological markers in a sample using chemical, optical, electrical, or other means. For example, such automatic sample analysis devices and automatic sample analysis systems may analyze a biological sample using immunoassays (e.g., antibody assays) or other assays directed at polypeptides, or using nucleic acid assays, or using general chemistry assays, or combinations thereof, in addition to the cytometric assays disclosed herein.

This Summary is provided to introduce a selection of concepts in a simplified form that are further described below in the Detailed Description. It should be understood that embodiments in this disclosure may be adapted to have one or more of the features described in this disclosure. This Summary is not intended to identify key features or essential features of the claimed subject matter, nor is it intended to be used to limit the scope of the claimed subject matter.

BRIEF DESCRIPTION OF THE DRAWINGS

FIG. 2A illustrates an imaging device with a sample and magnetic particles within a plurality of channels, prior to application of a magnetic field. The small dots shown over the windows represent magnetic particles. The magnetic particles are attached to cells in the sample.

FIG. 2B illustrates an imaging device with a sample and magnetic particles within a plurality of channels, prior to application of a magnetic field. The small dots shown over the windows represent magnetic particles dispersed throughout the volume of the chamber. The magnetic particles are attached to cells in the sample. The cross-section is taken along the line 2B shown in FIG. 2A.

FIG. 2C illustrates an imaging device with a sample and magnetic particles within a plurality of channels, following application of a magnetic field. The small dots shown over the window represent magnetic particles. The magnetic particles are attached to cells in the sample, and have drawn the cells to the window, adjacent the source of the magnetic field.

FIG. 2D illustrates an imaging device with a sample and magnetic particles within a plurality of channels, following application of a magnetic field. There are no small dots shown in FIG. 2D, illustrating the removal of the magnetic particles and cells from the bulk of the fluid sample within the chamber, and illustrating the placement of the magnetic particles and attached cells onto the surface of the window, where they have been drawn by the magnetic field, adjacent the source of the magnetic field. The cross-section is taken along the line 2D shown in FIG. 2C.

DETAILED DESCRIPTION

Figure 1A:
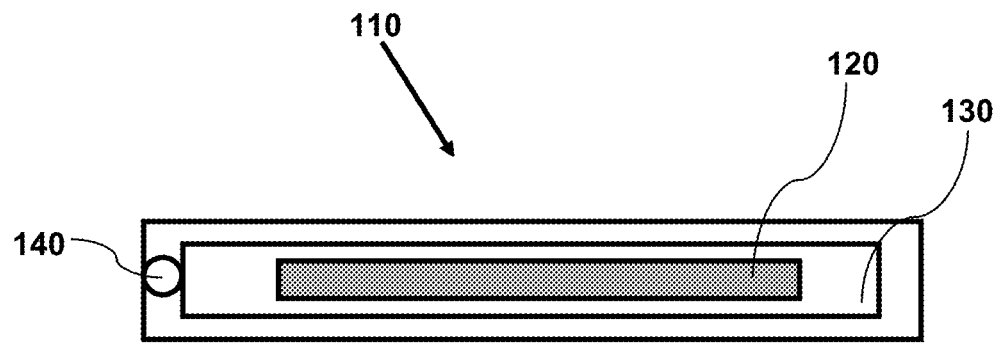
FIG. 1A shows a top view schematic illustration of an imaging device having features as disclosed herein, including a channel for containing a fluid sample, and a window coated with an adhesion agent.

Embodiments of devices, systems, and methods for cell analysis may be found, for example, in U.S. Pat. No. 8,380,541; U.S. Pat. App. Ser. No. 61/675,811, filed Jul. 25, 2012; U.S. Patent Application 61/837,168, filed Jun. 19, 2013, entitled "METHODS AND DEVICES FOR SMALL VOLUME LIQUID CONTAINMENT"; U.S. Patent Application 61/837,167, filed Jun. 19, 2013, entitled "METHODS AND DEVICES FOR SAMPLE ANALYSIS"; U.S. Pat. App. Ser. No. 61/676,178, filed Jul. 26, 2012; U.S. Pat. App. Ser. No. 61/766,116, filed Feb. 18, 2013; U.S. Pat. App. Ser. No. 61/802,194, filed Mar. 15, 2013; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; U.S. application Ser. No. 13/945,202, filed Jul. 18, 2013; U.S. application Ser. No. 13/951,063, filed Jul. 25, 2013; U.S. application Ser. No. 13/951,449, filed Jul. 25, 2013; U.S. application Ser. No. 14/161,639, filed Jan. 22, 2014; and U.S. application Ser. No. 14/167,964, filed Jan. 29, 2014, the disclosures of which patents and patent applications are all hereby incorporated by reference in their entireties.

Applicant provides devices, systems and methods for imaging fluid biological samples under microgravity conditions. Optical imaging techniques typically require that the object or objects to be imaged remain stationary for sufficiently long periods of time in order to obtain useful images. Since objects do not fall or settle under microgravity conditions, methods developed under normal gravity, which typically require freely floating objects to settle to a bottom surface, will not be useful or effective under microgravity conditions. Accordingly, the present devices, systems and methods provide means for imaging fluid biological samples without reliance on gravitational means for immobilizing cells, particles, crystals, or other constituents of fluid biological samples. (The term "cells" will be understood to refer collectively to cells, particles, crystals, and other constituents of fluid biological samples.)

Applicant discloses herein that cells in a fluid biological sample may be positioned in an imaging apparatus for imaging under microgravity conditions by: immobilizing the cells onto an imaging surface; moving cells under the influence of a magnetic field; constraining the cells within a small space so that the cells are in position for imaging; moving cells to an imaging surface by centrifugation; and combinations thereof. In these ways, cells of a fluid biological sample may be localized in a single focal plane, or within a focal region or volume effective to allow imaging of the cells. Methods, systems, and devices disclosed herein for positioning cells in fluid biological samples for imaging under microgravity may also be used under normal gravity conditions. Methods, systems, and devices disclosed herein for immobilizing cells in fluid biological samples for imaging under microgravity may also be used under normal gravity conditions.

Definitions

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like.

It is further noted that, as used in the specification and the appended claims, "or", as used in "A or B", refers to each of A; B; and A and B; that is, use of the word "or" includes "and/or" unless the context or an explicit statement clearly dictates otherwise. Thus, for example, reference to "treatment of cells or substrate" may include treatment of cells alone; treatment of substrate alone; and treatment of both cells and substrate.

References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, "gravity" refers to the acceleration due to the mass of the Earth (or, where relevant, other celestial object such as, e.g., the sun, the moon, or a planet).

As used herein, "one g", and "g" refer to the acceleration due to the Earth's gravitation field. One g is approximately equal to 9.8 m/sec$^2$ (32 feet/sec$^2$); under normal gravity conditions, the acceleration due to gravity is one g. Centrifugal force is also measured with respect to "g". When referring to centrifugal force, a force equal to 1×g corresponds to the force exerted by a mass under the influence of normal gravity (i.e., approximately equal to 9.8 m/sec$^2$ (32 feet/sec$^2$)); a force equal to 100×g corresponds to the force exerted by a mass under the influence of one hundred times normal gravity; a force equal to 1000×g corresponds to the force exerted by a mass under the influence of one thousand times normal gravity; and so forth.

As used herein, the "force of gravity" refers to the force experience by an object due to its presence on Earth. The magnitude of the force of gravity experiences by an object is determined by the mass of that object multiplied by the acceleration due to Earth's mass (this force is also termed the object's "weight").

As used herein, "microgravity" refers to conditions where the effective force of gravity acting on an object is very small as compared to the force of gravity that would affect the object when the object is at rest or moving at constant velocity on or near the surface of the earth. Under microgravity conditions, the force experienced by a mass is less than, and typically much less than, the force experienced by that mass under normal gravity conditions. A falling object near the surface of the earth experiences microgravity; hence, the term "free-fall" is sometimes used to refer to that form of microgravity. An object in orbit around the earth or other celestial body experiences microgravity. An object en route between celestial bodies, not subject to imposed accelerations (as occur, e.g., during firing of a rocket motor) experiences microgravity. Thus, microgravity conditions may be found, for example, in orbit around the Earth, or in free fall during travel along a trajectory between one astronomical object to another. Microgravity conditions may be produced near to Earth, for example, by falling from a height; or by travel (typically in an aircraft) along a parabolic pathway in which, for at least a portion of the pathway, the vehicle allows its passengers and contents to "free fall" within the vehicle. Objects experience little or no gravitational force in microgravity, and their motion is not significantly affected or directed by gravity under such conditions. Thus, objects at rest in microgravity do not fall, nor do particles within liquids settle to any significant extent, in the absence of the exertion of another force acting on the objects.

As used herein, the phrases "transportable device for imaging cells from a fluid biological sample", "a transportable device for imaging cells", "device for imaging cells from a fluid biological sample", "device for imaging cells", "imaging device", "imaging device for imaging cells", and grammatical equivalents thereof refer to devices configured to contain a fluid biological sample within a region adjacent to a window suitable for imaging cells or particles in the sample. Such a region may be a chamber or channel, at least one wall (or portion thereof) of which includes the window. The window is, or includes, an optically transmissive portion suitable for imaging cells or particles on or adjacent to an inner surface (or substrate) of the window. The face of the window contacting the biological sample is termed the internal, or inner, face of the window. The face of the window opposite the internal face is termed the external, or outer, face of the window. Optical elements (including, for example, lenses, light sources, and other optical elements) are positioned so that light may be transmitted and collected through the window; these optical elements are external to the chamber, and are typically positioned near to the external face of the window.

As used herein, a "cuvette" is a device configured for holding a fluid biological sample during optical imaging or microscopy directed at the sample or at cells within the sample. As used herein, a cuvette is configured for use with light sources, lenses, filters, optical detectors, and other optical devices and equipment effective to provide images and optical information suitable for identifying or characterizing cells in a fluid biological sample. A cuvette typically has one or more optically flat surfaces, and typically comprises optically transparent or translucent materials.

As used herein, the term "biological sample" refers to a fluid, tissue, or other material collected from a subject. A biological sample may be a fluid biological sample. A fluid biological sample may include fluid and some or all of cells, particles, crystals, and other components in the fluid. Examples of biological samples include but are not limited to, blood, serum, plasma, bone marrow, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk and/or other secretions or excretions. Biological samples may include nasopharyngeal wash, or other fluid obtained by washing a body cavity or surface of a subject, or by washing a swab following application of the swab to a body cavity or surface of a subject. Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone. The sample may be obtained from a human or animal. The sample may be obtained from a vertebrate, e.g., a bird, fish, or mammal, such as a rat, a mouse, a pig, an ape, another primate (including humans), a farm animal, a sport animal, or a pet. The sample may be obtained from a living or dead subject. The sample may be obtained fresh from a subject or may have undergone some form of pre-processing, storage, or transport.

The terms "blood" and "whole blood" refer to blood as it exists within an animal and as directly obtained from a subject in a blood sample. Blood contains red blood cells, white blood cells, proteins such as albumin, globulins, and clotting factors, salts, water, and other constituents. A blood sample is a fluid biological sample.

The terms "plasma" and "blood plasma" refer to the liquid portion of blood (e.g., a blood sample) that remains after the removal of blood cells. Red blood cells and white blood cells may be removed by centrifugation of a blood sample, leaving plasma above the pelleted cells in the bottom of the centrifuge tube. Plasma retains blood clotting factors, and is obtained from anti-coagulated blood samples. A sample of plasma is a fluid biological sample.

The terms "serum" and "blood serum" refer to the liquid portion of blood that remains after blood is allowed to clot, and the clot is removed. Serum differs from plasma in that serum lacks clotting factors: since clotting requires fibrin, thrombin, and other proteins, which form and remain part of a blood clot, serum lacks these proteins while plasma contains them. A sample of serum is a fluid biological sample.

As used herein, a "finger-stick" refers to: i) the act of making a small puncture in the skin of a subject, allowing a small amount (e.g., a droplet, or one, two, or a few drops) of blood to flow and become available for collection; ii) the puncture itself; and iii) the blood collected thereby. Blood may be liberated in a finger-stick, for example, by use of a lancet or other sharp implement effective to pierce the skin of a subject. Typically, only a small amount of blood is collected in this way (e.g., the amount of blood may be about 250 µL or less, or about 200 µL or less, or about 150 µL or less, or about 100 µL or less, or about 50 µL or less, or about 25 µL or less, or about 15 µL or less, or about 10 µL or less, or about 10 µL or less, or about 5 µL or less, or about 3 µL or less, or about 1 µL or less). Blood from a finger-stick may be collected, e.g., by needle, syringe, capillary tube, or other method. Blood from a finger-stick may be collected for transport to another location; for storage prior to use or analysis; for immediate use; or for a combination of the same.

As used herein, a "sample", such as a fluid biological sample, may be of any suitable size or volume, and is preferably of small size or volume. In some embodiments of the devices and methods disclosed herein, measurements may be made using a small volume sample, or no more than a small volume portion of a sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, "cells", "cells and particles" and "cells or particles" refer to all objects of interest in a fluid biological sample, including cells, crystals, bacteria, viruses, cell debris, fibers, and other material which may be found in a fluid biological sample. The term "cells" will be understood to refer collectively to "cells and particles" as defined above unless explicitly stated otherwise, or unless the context makes clear that what are referred to are cells alone, and not all objects of interest in a fluid biological sample.

The terms "adhesion agent" and "adhesion agents" as used herein refer to an agent, or plurality of agents, applied to a device surface, to a cell, or both, which aids or effects binding of a cell to a device surface, such as a cell from within a fluid biological sample to an internal surface of a cuvette (such as an internal surface of a window or other surface). The term "adhesion agents", e.g., as used in the phrase "a coating of adhesion agents" or the like, may refer to multiple numbers of the same type of adhesion agent, to multiple types of different adhesion agents, or both (e.g., to a coating containing multiple numbers each of different types of adhesion agents).

An adhesion agent may be any molecule or multi-molecular structure that is capable of immobilizing a cell to the internal surface of a cuvette. An adhesion agent can be an antibody, antibody fragment, or antibody mimic (e.g., antibodies and antibody fragments which specifically bind epitopes known to be present on proteins or other molecules on the surface of cells to be immobilized); a polypeptide (e.g., albumin, poly-L-lysine or other amino acid homopolymer, collagen, fibrin, fibronectin, cell adhesion molecules such as vascular cell adhesion molecule (VCAM), epithelial cell adhesion molecule (EpCAM), intercellular adhesion molecule (ICAM), and neural cell adhesion molecule (NCAM), or other polypeptides which may bind cells); a lectin (e.g., a concanavalin or other lectin); a polymer (e.g., polyethylene glycol (PEG), including PEG copolymers and block copolymers, and PEGylated polypeptides such as PEG-polyl-L-lysine and others); a glue (e.g., epoxy glues, acrylate glues, and other glues); a resin; a lipid (e.g., phosphatidyl choline, phosphatidyl ethanoline, cholesterol, stearic acid, and other lipid molecules normally present in cell membranes, and conjugates containing such lipids); a polynucleotide; a nucleic acid analog (e.g., a peptide nucleic acid or a locked nucleic acid); an oligosaccharide; a polysaccharide (e.g., agar, or a derivative thereof); a cell receptor; an immunoadhesin; a ligand; biotin; avidin or streptavidin; a fragment or derivative thereof, and combinations thereof. An adhesion agent can be attached to the internal surface of a cuvette either covalently or non-covalently by any suitable method.

As used herein, the terms "peptide", "polypeptide", "protein", and the like are used interchangeably to refer to compounds composed of sequences of two or more amino acids covalently linked by peptide bonds; these compounds may also include covalently linked sugars, labels (e.g., fluorescent or enzyme labels), polymers (e.g., polyethylene glycol), and other constituents and substituents as well as the amino acid chain which identifies such compounds as polypeptides.

The term "antibody" is used in the broadest sense and specifically covers monoclonal antibodies and polyclonal antibodies (compositions with polyepitopic specificity). Monoclonal antibodies are obtained from a population of substantially homogeneous antibodies, i.e., the individual antibodies comprising the population are identical except for possible naturally-occurring mutations that may be present in minor amounts.

As used herein, the terms "antibodies" includes "antibody fragments." An antibody fragment comprises a polypeptide having a primary structure consisting of one uninterrupted sequence of contiguous amino acid residues having the amino acid sequence of an intact antibody. Examples of antibody fragments include Fab, Fab', Fab'-SH, F(ab')$_2$, Fd, Fc, Fv, diabodies, and any other "Non-single-chain antigen-binding unit" as described, e.g., in U.S. Pat. No. 7,429,652. As used herein, an "antigen-binding antibody fragment" is any antibody fragment that retains the ability to bind to the specific target to which the intact antibody specifically binds. An antigen-binding antibody fragment may have different (e.g., lesser) binding affinity for the target antigen than the intact antibody.

The term "immunoadhesin" designates an antibody-like molecule which combines a polypeptide binding specificity portion covalently linked to an immunoglobulin constant domain. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG4 subtypes, IgA (including IgA-1 and IgA-2), IgE, IgD or IgM. The production of immunoglobulin fusions is discussed in U.S. Pat. No. 5,428,130.

The terms "target", "target molecule", "target polypeptide", and the like are used herein to denote the surface characteristic of a cell, particle, or other target that is bound by an adhesion agent.

The terms "antigen", "target epitope", and the like are used herein to denote the molecule or portion thereof that is specifically bound by an antibody or antibody fragment. These terms "antigen", "target epitope", and the like are specific examples of "targets", "target molecules", "target polypeptides" and the like, for an antibody of antibody fragment.

As used herein, the terms "magnetic bead" and "magnetic particle" refer to small magnetic, ferromagnetic, paramagnetic, or magnetizable particles which may be coated with adhesion agents to bind target analytes or cells, and, under the influence of a magnetic field, maneuver the bound target analytes or cells to a desired location. Magnetic beads may be made of polystyrene, agarose, metals (typically coated, e.g., with carbon or carbon compounds), or other materials. Magnetic particles may be coated with antibodies, nucleic acids, lectins, biotin, avidin, streptavidin, or other agents which may bind target analytes or cells. Magnetic particles are commercially available; magnetic particles, for example, sold under the trade mark DYNABEADS® are available from Life Technologies (Grand Island, N.Y., USA); PureProteome™ particles are available from Millipore; magnetic particles are available from other suppliers as well.

As used herein, the term "imaging" refers to any and all forms of optical measurements, including microscopy, fluorescence measurements, light scattering measurements, polarization measurements, and other optical measurements. For example, imaging includes measuring the intensity of light, typically at a particular wavelength or within a wavelength range. For example, such imaging measurements may include measurement of fluorescence emitted following excitation of an object by light shined on the object; such imaging measurements may include measurement of light scattered by an object illuminated by light shined on the object; and may include other measurements. Imaging may include formation of, measurement of, or recording of, an image of an object by optical means.

As used herein, an "attachment element" refers to a feature configured to engage a transport element or component; thus an attachment element may be or include a receptacle, a recess, a handle, a tab, a post, a ring, a hook, a slot, a magnet, a ferromagnetic (e.g., a suitable metal) or paramagnetic element configured to engage with a magnet, or other element that may be used to manipulate (e.g., to grab or clamp) a component having the attachment element. For example, engagement between an attachment element and its counterpart may be effected by mechanical, friction, pressure, suction, magnetic, electrostatic, adhesive, or other means. A transport mechanism may engage an attachment element on a device in order to carry the device from one location to another. An attachment element is suitable for engaging a transportable device, such as an imaging device as disclosed herein, for transport by a transport system, and is suitable for securing the transportable device (e.g., an imaging device) in a location suitable for imaging, for use in the performance of assays, or for other purposes.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

Transport Systems

A transport system may be used to move components, devices, or other parts and materials from one location to another, e.g., from one location to another within a device or within a housing of a device or system. In embodiments, a transport system may move components, devices, or other parts and materials from one location to another within a system or within a housing enclosing a system.

A transport system may have other capabilities or uses; for example a transport system may comprise a dual-use system including, for example, fluid transport capabilities as well as transport capabilities. For example, a fluid transport system may comprise a dual-use system having transport capabilities as well as fluid transport capabilities.

In embodiments, a transport system as disclosed herein may comprise a fluid handling system or a fluid handling device. In embodiments, such a fluid handling system may comprise a pipette nozzle. In embodiments, a pipette nozzle may engage, and may be used to transport, a device, component, or element, such as, e.g., a transportable device for imaging cells (e.g., a cuvette) as disclosed herein. In embodiments, mechanisms, methods, or elements for engaging and transporting a tip (e.g., a pipette tip, or other cylindrical or conical component, typically comprising an open end or two open ends) from one location to another may also be used to engage and to transport a transportable device for imaging cells as disclosed herein. For example, a pipette nozzle may be used for engaging and transporting a tip. Disclosure regarding a fluid handling device, a fluid handling system, or other such devices or systems applies equally to transport of a transportable device for imaging cells as disclosed herein as to any other device, component, or element.

A fluid handling device may be configured to interface with a tip, or any other component. For example, a fluid handling device may be configured to interface with a transportable device for imaging cells (e.g., a cuvette). A fluid handling device may include a pipette nozzle, which may be press-fit to a pipette tip or to an attachment element of a transportable device for imaging cells (e.g., a cuvette). Additional mechanisms may be used to connect a tip or other component to the fluid handling device including, but not limited to, magnetic, snap-fit, hook and loop fasteners, elastics, ties, sliding mechanisms, locking mechanism, clamps, actuated mechanical components, and/or adhesives. The connection of a component (e.g., a cuvette) or tip may permit the fluid handling device to function as a robot capable of performing one or more fluid-handling or non-fluid handling functions. Such functions may include the ability to transfer a transportable device for imaging cells (e.g., a cuvette) from one location to another.

A pipette nozzle may be capable of interfacing with a tip, or a transportable device for imaging cells (e.g., a cuvette).

For example, specific pipette nozzles may be configured to interface with specific tips or components. Alternatively, a single pipette nozzle may be capable of interfacing with a plurality of tips or components. A pipette nozzle may be capable of interfacing with tips or components having different configurations, dimensions, volume capacities, materials, and/or size. In embodiments, a pipette nozzle may be configured to, and may be capable of, engaging with a transportable device for imaging cells from a fluid biological sample.

In embodiments, an attachment element may include, or be configured to engage, one or more rotational mechanism such as a screw, bolt, nut, or other element. For example, an attachment element including a rotational mechanism may be used to engage a tip, or to engage a transportable device for imaging cells from a fluid biological sample. Such rotational mechanisms may include screwing a tip onto a pipette nozzle. In embodiments, a tip, or a transportable device for imaging cells from a fluid biological sample may connect to a pipette nozzle or other element of a transport device via press-fit, magnetic coupling, or any other attachment element. In additional embodiments, a portion of the tip surface, or a portion of a transportable device for imaging cells from a fluid biological sample may embed in an interface, or a portion of an interface may be embedded within a tip or transportable device for engagement. Features which may aid in such engagement include flanges, grooves, protrusions, ridges, bumps, depressions, and other features.

A pipette nozzle, cuvette, or other component may have one, two or more flanges, or other surface features described elsewhere herein. A collar may fit over an element of a tip or a transportable device for imaging cells (e.g., a cuvette). An O-ring may fit over or engage with an element of a tip or a transportable device for imaging cells. A tip or a transportable device for imaging cells may have one or more grooves, e.g., for engaging with an O-ring. A high-friction and/or flexible material may be provided between a portion of the nozzle and tip or a transportable device for imaging cells, e.g., suitable for enabling a press-fit engagement. Engagement with a tip, or a transportable device for imaging cells from a fluid biological sample may use one or more features, characteristics, or methods disclosed herein.

Devices, Systems, and Methods

Devices, assays, methods, and systems for imaging cells from a fluid biological sample may be used in, or with, other devices and systems. For example, a device for imaging cells from a fluid biological sample may be part of, or used with, a device or system which is capable of performing other assays and analysis of a fluid biological sample, including other assays and analysis of cells from a fluid biological sample, or including other assays and analysis of analytes in a fluid biological sample. For example, a system for the analysis of a fluid biological sample may include a cytometry station and may include other stations or modules, such as, e.g., a general chemistry module; a nucleic acid analysis module; an immunoassay module; or other module or modules.

Such devices, systems, and methods may be used under microgravity conditions. Devices, assays, methods, and systems for use in microgravity may be used in, or with, other devices and systems. For example, a device for imaging cells from a fluid biological sample may be part of, or used with, a device or system which is capable of performing other assays and analysis of a fluid biological sample, including other assays and analysis of cells from a fluid biological sample, or including other assays and analysis of analytes in a fluid biological sample. For example, a system for the analysis of a fluid biological sample may include a cytometry station and may include other stations or modules, such as, e.g., a general chemistry module; a nucleic acid analysis module; an immunoassay module; or other module or modules.

Cytometry

Cytometry assays are typically optical measurements and assays used to measure characteristics of individual cells. In embodiments, more than one cell, and often many cells, may be measured at one time or in rapid succession. The cells being monitored may be live or dead cells. By using appropriate dyes, stains, or other labeling molecules, cytometry may be used to determine the presence, quantity, or modifications of specific proteins, nucleic acids, lipids, carbohydrates, or other molecules. Properties that may be measured by cytometry also include measures of cellular function or activity, including but not limited to phagocytosis, active transport of small molecules, mitosis or meiosis; protein translation, gene transcription, DNA replication, DNA repair, protein secretion, apoptosis, chemotaxis, mobility, adhesion, antioxidizing activity, RNAi, protein or nucleic acid degradation, drug responses, infectiousness, and the activity of specific pathways or enzymes. Cytometry may also be used to determine information about a population of cells, including but not limited to cell counts, percent of total population, and variation in the sample population for any of the characteristics described above. Cytometric assays may be used to measure one or more of the above characteristics for each cell, which may be advantageous to determining correlations or other relationships between different characteristics. Cytometric assays may also be used to independently measure multiple populations of cells, for example by labeling a mixed cell population with antibodies specific for different cell lines.

Cytometry may be useful for determining characteristics of cells in real-time. Characteristics of cells may be monitored continuously and/or at different points in time. The different points in time may be at regular or irregular time intervals. The different points in time may be in accordance with a predetermined schedule or may be triggered by one or more event. Cytometry may use one or more imaging or other sensing technique described herein to detect change in cells over time. This may include cell movement or morphology. Kinematics or dynamics of a sample may be analyzed. Time series analysis may be provided for the cells. Such real-time detection may be useful for calculation of agglutination, coagulation, or prothrombin time. The presence of one or more molecule and/or disease, response to a disease and/or drug, may be ascertained based on the time-based analysis.

Examples of cytometric analysis include flow cytometry, microscopy, and other analysis. Flow cytometry typically uses a mobile liquid medium that sequentially carries individual cells to an optical detector. Microscopy typically uses optical means to detect stationary cells, generally by recording at least one magnified image. It should be understood that flow cytometry and microscopy are not entirely exclusive. As an example, some flow cytometry devices and assays use microscopy to record images of cells passing by the optical detector. Many of the targets, reagents, assays, and detection methods may be the same for flow cytometry and microscopy. As such, unless otherwise specified, the descriptions provided herein should be taken to apply to these and other forms of cytometric analyses known in the art.

In some embodiments, up to about 10,000 cells of any given type may be measured. In other embodiments, various numbers of cells of any given type are measured, including, but not limited to, more than, and/or equal to about 10 cells, 30 cells, 50 cells, 100 cells, 150 cells, 200 cells, 300 cells, 500 cells, 700 cells, 1000 cells, 1500 cells, 2000 cells, 3000 cells, 5000 cells, 6000 cells, 7000 cells, 8000 cells, 9000 cells, 10000 cells, or more.

In some embodiments, cytometry is performed in microfluidic channels. For instance, flow cytometry analyses are performed in a single channel or in parallel in multiple channels. In some embodiments, flow cytometry sequentially or simultaneously measures multiple cell characteristics. In some instances, cytometry may occur within one or more of the tips/vessels described herein. Cytometry may be combined with cell sorting, where detection of cells that fulfill a specific set of characteristics are diverted from the flow stream and collected for storage, additional analysis, and/or processing. Such sorting may separate multiple populations of cells based on different sets of characteristics, such as 3 or 4-way sorting.

A cytometry station may include a cytometer for performing cytometry on a sample, as described above and in other embodiments of the invention. The cytometry station may perform cytometry on a sample while one or more other modules of system for analyzing cells from a fluid biological sample perform other preparation and/or assaying procedure on another sample. In some situations, the cytometry station may perform cytometry on a sample after the sample has undergone sample preparation in one or more other modules (e.g., general chemistry module; nucleic acid analysis module; immunoassay module; or other module).

Cuvettes

Transportable devices for imaging cells from a fluid biological sample in microgravity include means for accepting a fluid biological sample, or portion thereof. Transportable devices for imaging cells from a fluid biological sample in microgravity are also termed "imaging devices. Such transportable devices, and such imaging devices, may also be useful for imaging cells in fluid biological samples under conditions that are not microgravity conditions; for example, such transportable devices, and such imaging devices, may also be useful for imaging cells in fluid biological samples under normal gravity conditions. Transportable devices for imaging cells from a fluid biological sample include a window, or windows, suitable for imaging of the biological sample or portion thereof. Transportable devices for imaging cells from a fluid biological sample include a chamber, a channel, or both, or a plurality of chambers or channels, suitable for holding the biological sample or portion thereof. At least one window of a transportable device for imaging cells forms at least part of a wall of a channel or of a chamber. Transportable devices for imaging cells from a fluid biological sample include an attachment element, or a plurality of attachment elements, configured for engaging a transport system. In embodiments, a transportable device for imaging cells may comprise a cuvette. Such a cuvette may be configured for engaging a transport system.

Thus, transportable devices for imaging cells from a fluid biological sample include a port, or a plurality of ports, through which a fluid biological sample may be introduced into the device. Transportable devices for imaging cells from a fluid biological sample include a chamber, or a channel, or both, in fluid communication with a port, or plurality of ports, effective that a fluid biological sample introduced into a port may flow into a chamber or channel; in embodiments, a fluid biological sample introduced into a port may flow via a channel into a chamber. In embodiments, a transportable device for imaging cells may include a plurality of chambers or channels. Each chamber and each channel of a transportable device for imaging cells is in fluid communication with at least one port, either directly or indirectly via another chamber or channel.

In embodiments, a transportable device for imaging cells includes one or more attachment elements configured to engage a transport system. For example, a transportable device for imaging cells may include a recess configured to accept a pipette nozzle effective that the nozzle (as part of a transport system) may be used to transport the transportable device from one location to another. In embodiments, a transportable device for imaging cells may comprise a cuvette. Such a cuvette may be configured for engaging a transport system.

In embodiments, a cuvette comprises a chamber configured for imaging cells, such as cells from a fluid biological sample. In embodiments, a cuvette may comprise a plurality of chambers configured for imaging cells, such as cells from a fluid biological sample. In embodiments, a cuvette may comprise one, two three, four, five, six, seven, eight, nine, ten, fifteen, twenty, or more chambers configured for imaging cells. A chamber will include at least one optically transmissive internal surface (where an internal surface faces, and typically contacts, a fluid biological sample within the cuvette).

Thus, transportable devices for imaging cells from a fluid biological sample include a window through which cells may be imaged. A window, or windows, included in transportable devices for imaging cells from a fluid biological sample typically comprises an optically transmissive external surface (e.g., facing a lens, illumination source, filter, or other optical element) suitable for admitting or passing light and for obtaining an image of objects contained within the device. A window has an external surface (typically facing or closest to a source of illumination) and an internal surface (typically facing an internal chamber of a cuvette). A window, or windows, included in transportable devices for imaging cells from a fluid biological sample typically comprises an optically transmissive internal surface in contact with the biological sample (e.g., forming at least a portion of a wall of a chamber or channel in which the biological sample is present) suitable for admitting or passing light and for obtaining an image of the biological sample.

A window may be made of glass, or of a plastic, or other material. A glass window may be made of borosilicate glass, or sodium silicate glass, or aluminosilicate glass, or quartz, or other glass. A plastic window may be made of polystyrene, polyethylene, polypropylene, polycarbonate, polyolefin, polyvinyl chloride, polyurethane, a polyester, a polyamide, a polyimide, a polysulfone, a polyphenylene, an acrylic, or other plastic. A window may be made of a cellulosic material. A window may include a mixture of materials.

Where a window includes a coating, the window may be treated to enhance binding of the coating, or for other reasons, prior to, during, or after application of the coating. For example, a window may be washed with water or other aqueous solution; or may be treated with an acid; or may be treated with a base; or may be otherwise treated during fabrication or before use.

In embodiments, a chamber or channel is configured to immobilize cells for imaging. For example, a chamber may be configured to immobilize cells in a particular location conducive to imaging; in embodiments, any location and all locations within a chamber may be suitable for imaging cells from a fluid biological sample. Such immobilization may be due, at least in part, to adhesion of cells to a wall of the chamber or channel; to positioning of cells at or near a wall of the chamber or channel under the influence of a magnetic field; to physical constraint of the cells within a small chamber or channel; or a combination of these. In embodiments, application of centrifugal force (e.g., due to centrifugation) may direct cells to a window, and may aid such immobilization as well.

For example, in embodiments, a chamber of an imaging device as disclosed herein may include a narrow channel or channels having a height of the order of a cell diameter (e.g., a shallow channel with a height of between about 15 to about 50 micrometers (μm)). Flow of a fluid sample into and within such a narrow chamber may be regulated so that cells in the sample have time to bind to an internal surface of the chamber. In embodiments, the internal surface is coated, or treated, so as to retain cells. In embodiments, the coated or treated surface comprises an optically transparent surface suitable for imaging cells on or near to the surface (e.g., a window). Such binding of cells of the sample to an internal surface of the chamber is effective to attain a higher density of cells in the chamber (e.g., attached to an internal surface of the chamber) than was originally present in the sample before it flowed into and within the chamber, and may result in fluid exiting from the chamber that has reduced numbers, or is devoid of, cells. A chamber may have an exit port configured to retain cells within the chamber (e.g., an exit port porous to fluid but substantially non-porous to cells, such as a mesh, a net, a plurality of very small channels, or other features suitable for retaining cells within the chamber).

In embodiments, immobilizing cells on or near to a wall of a chamber (e.g., a channel) for imaging may include allowing, or causing, a fluid sample to dry effective that cells may become attached to an internal surface of a chamber, suitable for imaging. Drying of a fluid sample leaves cells in a thin film on an internal surface of a chamber, and in suitable locations for imaging. Drying may lead to partial dryness of the sample (e.g., where a layer of fluid remains), or may lead to substantially complete dryness of the sample (e.g., where only a minimal amount of fluid remains). Drying of a fluid sample in order to leave cells in suitable locations for imaging may be performed at room temperature (e.g., between about 18 to about 22° C.), or at elevated temperature ((e.g., above about 22° C.). Drying of a fluid sample in order to leave cells in suitable locations for imaging may be aided by reducing air pressure (e.g., partial or other vacuum). Drying of a fluid sample in order to leave cells in suitable locations for imaging using vacuum may be performed at any suitable temperature, including reduced (e.g., below about 18° C.), elevated, or other temperature. Such cell immobilization including drying may be used alone, and may be used along with any means or method for immobilizing cells for imaging disclosed herein.

In embodiments, positioning of cells near to, or on an internal surface of a cuvette chamber or channel (e.g., a window) aids in imaging the cells. In embodiments, immobilizing cells, on an internal surface of a cuvette chamber or channel aids in imaging the cells. For example, providing that most or all cells are positioned in a particular location, area, or region (e.g., near an internal surface of a chamber) allows better and more consistent imaging (e.g., better focusing or other optical consideration) in that position. For example, cells positioned near an internal surface of a chamber may be better focused in that position.

In embodiments, a device having features disclosed herein may be configured to provide both epi-illumination and trans-illumination of a sample within a chamber, where the illumination originates from only a single side of the device, and where epi-illumination comprises light traveling from said illumination source to said sample without reflection at a surface of the optically transmissive material of the sample holder, and where trans-illumination comprises light traveling to the sample following at least one reflection from at least one surface of said device. In embodiments, the external source of illumination responsible for epi-illumination and trans-illumination is disposed near to a window of the device. In embodiments, that least one of epi-illumination and trans-illumination comprises an internal reflection of light. In embodiments, that least one of epi-illumination and trans-illumination comprises multiple internal reflections of light. In embodiments, at least one of epi-illumination and trans-illumination comprises an internal reflection of light from at least one surface of said device. In embodiments, at least one of epi-illumination and trans-illumination comprises multiple internal reflections of light from at least one surface of said device. In embodiments, that least one of epi-illumination and trans-illumination comprises a total internal reflection of light. In embodiments, that least one of epi-illumination and trans-illumination comprises multiple total internal reflections of light. In embodiments, said trans-illumination is provided at least in part by an internal reflection of light at a surface of the device. In embodiments, said trans-illumination is provided at least in part by multiple internal reflections of light from at least one surface of the device. In embodiments, said trans-illumination is provided at least in part by total internal reflection of light at a surface of the device. In embodiments, said trans-illumination is provided at least in part by multiple total internal reflections of light from at least one surface of the device.

Imaging Devices with Windows which Bind Cells

In embodiments, an internal wall of a chamber is configured to immobilize cells. In embodiments, more than one internal wall of a chamber is configured to immobilize cells. In embodiments, a chamber wall configured to immobilize cells comprises an optically transmissive surface. In embodiments, a chamber wall configured to immobilize cells comprises an optically transmissive internal surface. In embodiments, a chamber wall configured to immobilize cells comprises a wall having a surface parallel to an optically transmissive external surface. In embodiments, a chamber wall having a surface parallel to an optically transmissive external surface itself comprises an optically transmissive surface.

In embodiments, an internal surface of a chamber of a cuvette comprises an adhesion agent, wherein said adhesion agent is effective to immobilize cells within the chamber. Such immobilization aids imaging of the cells.

In embodiments, an adhesion agent may comprise an antibody, an antibody fragment, an antibody mimic, an immunoadhesin, a cell receptor, a ligand, a nucleic acid, a nucleic acid analog, a polypeptide, a polymer, a lectin, a lipid, an oligosaccharide, a polysaccharide, a glue, biotin, avidin, a derivative thereof, and combinations thereof.

In embodiments, an internal surface of a chamber of a cuvette comprises a magnetic bead suitable for adhering to cells. Such immobilization aids imaging of the cells.

In embodiments, a chamber or channel of a cuvette comprises dimensions close to the size of a typical cell found in a fluid biological sample, effective that such cells are constrained to be near to an inner wall of the chamber or channel. Such positioning of the cells aids imaging of the cells.

In embodiments, a channel of a cuvette may be an elongated channel, having a length and a width, where the length is greater than the width, and where the length and width are determined on a plane that is substantially parallel to the surface of a window of the cuvette (and so substantially perpendicular to an illumination light path through a window of the cuvette). In embodiments, the length of the channel is determined along an orientation substantially parallel to the direction of flow of a fluid biological sample when filling the channel, and the width of the channel is determined along an orientation substantially perpendicular to the direction of flow of a fluid biological sample when filling the channel.

In embodiments, the channel may have a vertical dimension (i.e., a dimension substantially parallel to the direction of light directed through the window at the sample within the channel) that is smaller than the length of the channel. In embodiments, the channel may have a vertical dimension that is smaller than the width of the channel. In embodiments, the channel may be an elongated channel, having a length greater than its width.

Figure 1B:
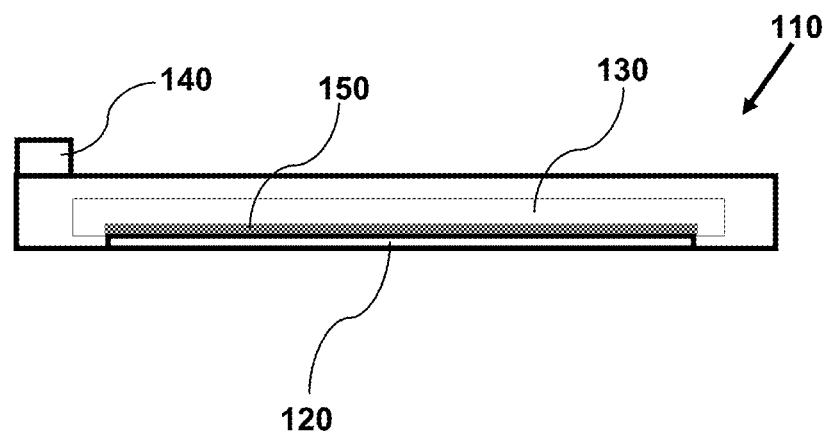
FIG. 1B shows a cross-sectional side view schematic illustration of an imaging device having features as disclosed herein, including a channel for containing a fluid sample, and a window coated with an adhesion agent.

As illustrated in FIG. 1A (top view) and FIG. 1B (cross-sectional side view), an imaging device 110 having features as disclosed herein may have a window 120 for imaging a fluid sample contained with an elongated channel 130 for containing a fluid sample. An elongated channel 130 may contain all of, or a portion of, a single fluid sample (e.g., an aliquot of a larger fluid sample may be contained within an elongated channel 130). In embodiments, an imaging device 110 may have an attachment element 140. For example, as illustrated in FIG. 1A and FIG. 1B, an attachment element 140 may be configured for engagement with a transport system. An attachment element 140 is suitable for engagement by a transport system effective to secure the imaging device 110 for transport, or for securing the imaging device 110 in a location suitable for imaging. The cross-sectional view shown in FIG. 1B is taken along a line running from right to left that bisects the attachment element 140 shown in FIG. 1A.

For example, an imaging device having features as disclosed herein may have a channel for containing a fluid sample, the channel having a window, where the window, or a portion of the window useful for imaging cells from a fluid biological sample contained within the channel, is coated with an adhesion agent. A window 120 coated with an adhesion agent 150 is illustrated in FIGS. 1A and 1B. It will be understood that illustrations of a coating of adhesion agent 150 (and illustrations of such coatings in other figures) is not intended to be drawn to scale, but instead to indicate the positioning of such a coating 150 on an interior surface of a window 120. The adhesion agent 150 is effective to immobilize at least a portion of the cells contained within the fluid biological sample; such immobilization aids in imaging those cells by holding them in position during imaging. A channel, such as an elongated channel, of an imaging device as disclosed herein has a vertical dimension (i.e., a dimension substantially parallel to the direction of light directed at the sample within the channel). Where the vertical dimension is large, a large number of cells may be disposed in a column within a volume having a base area and a (large) height, where the base area is an area on the interior face of the window having a size that is about the size of a spot of illumination directed onto the window of the channel, and the height is the vertical height of the channel as measured interior to the channel, i.e., ignoring the thickness of the channel walls). Where the vertical dimension is small, a small number of cells may be disposed in such a column within a volume having such a base area and such a small height.

In embodiments, a vertical dimension (height) of a chamber (e.g., a channel) may be about 250 micrometers ($\mu m$), or about 200 $\mu m$, or about 150 $\mu m$, or less. In embodiments, a vertical dimension (height) of a chamber (e.g., a channel) may be about 100 micrometers ($\mu m$) or less. In embodiments, a chamber (e.g., a channel) having a small vertical dimension (e.g., a narrow chamber or channel) may have a height of about 100 $\mu m$, or of about 75 $\mu m$, or of about 50 $\mu m$ or less. In embodiments, a narrow chamber or narrow channel may have a vertical dimension (height) of between about 8 $\mu m$ and about 100 $\mu m$, or between about 10 $\mu m$ and about 75 $\mu m$. In embodiments, a narrow chamber or narrow channel may have a height of between about 15 $\mu m$ and about 50 $\mu m$. In embodiments, a wide chamber or wide channel may have a vertical dimension (height) of between about 100 $\mu m$ and about 250 $\mu m$, or between about 125 $\mu m$ and about 225 $\mu m$. In embodiments, a wide chamber or wide channel may have a height of between about 150 $\mu m$ and about 200 $\mu m$.

A fluid biological sample disposed within a chamber, such as an elongated channel, having a small height provides a large percentage of cells within such a column that are in a proper position for imaging (i.e., are close enough to the focal plane or focal point of the imaging device for optimal imaging). A fluid biological sample disposed within a chamber, such as an elongated channel, having a small height is conducive to attachment of cells to a surface of the chamber; such a surface may be an optically transmissive surface (e.g., a window), whereby attachment of cells to that surface immobilizes the cells in a proper position for imaging (i.e., at or near to a focal plane or focal point of the imaging device for optimal imaging).

A fluid biological sample disposed within a chamber, such as an elongated channel, having a large height may provide more cells for imaging within such a column than would such a sample disposed within an elongated channel having a small height; however, many of the cells within the volume in the large height would be in a poor position for imaging (i.e., would not be close enough to the focal plane or focal point of the imaging device for optimal imaging). For this reason, even in a chamber having a large height, coating a surface (e.g., a window) with an adhesion agent, causing cells to adhere to the surface, and optionally flowing the sample across the surface multiple times to increase the probability of cell contact with the adhesion agent coating the surface, may increase the numbers of cells close enough to the focal plane or focal point of the imaging device for optimal imaging as compared to the numbers obtained in the absence of an adhesive coating.

For example, an imaging device having features as disclosed herein may have a plurality of channels for containing a fluid sample, each channel having a window, where the window, or a portion of the window useful for imaging cells from a fluid biological sample contained within the channel, is coated with an adhesion agent. An embodiment of such an imaging device is illustrated in FIG. 1C and FIG. 1D.

Figure 1C:
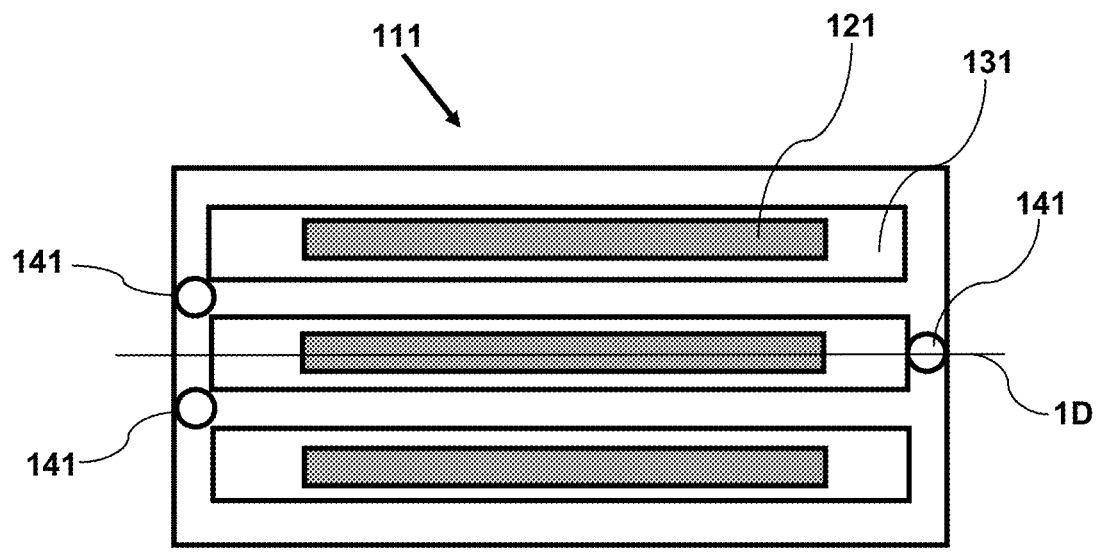
FIG. 1C shows a top view schematic illustration of an imaging device having features as disclosed herein, including a plurality of channels for containing a fluid sample, and a window (in each channel) coated with an adhesion agent.
Figure 1D:
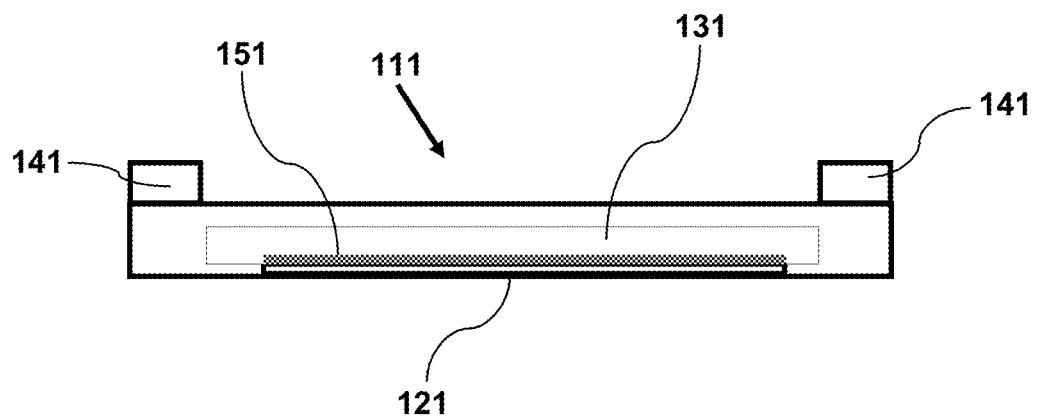
FIG. 1D shows a cross-sectional side view schematic illustration of an imaging device having features as disclosed herein, including a plurality of channels for containing a fluid sample, and a window (in each channel) coated with an adhesion agent. The cross-section is taken along the line 1D shown in FIG. 1C.

As illustrated in FIG. 1C (top view) and FIG. 1D (cross-sectional side view), an imaging device 111 having features as disclosed herein may have multiple windows 121 for imaging a fluid sample contained with elongated channels 131 for containing a fluid sample. As shown, an imaging device 111 may have multiple attachment elements 141. An attachment element 141 is suitable for engagement by a transport system effective to secure the imaging device 111 for transport, or for securing the imaging device 111 in a location suitable for imaging. The cross-sectional view shown in FIG. 1D is taken along a line that bisects the attachment element 141 shown at the right, and is mid-way between the two attachment elements 141 shown at the left, of FIG. 1C. Each elongated channel 131 has at least one window 121. Each window 121 is coated on an interior surface with an adhesive coating 151, as illustrated in FIGS. 1C and 1D. It will be understood (for this and for illustrations of such coatings in other figures) that this illustration of a coating of adhesion agent 151 is not intended to be drawn to scale, but instead to indicate the positioning of such a coating 151 on an interior surface of a window 121. An elongated channel 131 may contain all of, or a portion of, a single fluid sample (e.g., an aliquot of a larger fluid sample may be contained within an elongated channel 131). In embodiments, a single fluid sample may be apportioned between two or more of the elongated channels 131. In embodiments, two or more fluid samples, or aliquots thereof, may be contained in two or more elongated channels 131. For example, an imaging device as shown in FIGS. 1C and 1D having three elongated channels 131 may contain three separate fluid samples, or aliquots of three separate fluid samples, with a different fluid sample (or aliquot thereof) in each elongated channel 130. As shown in FIGS. 1C and 1D, each of the plurality of elongated channels 131 is fluidically separated from the other elongated channels 131; however, in embodiments, two or more elongated channels 131 may be in fluidic continuity with each other and may allow flow of fluid sample from one such elongated channel 131 to another such elongated channel 131. In embodiments, all of a plurality of elongated channels 131 may be in fluidic continuity with each other, allowing flow of fluid sample between all such elongated channels 131 in an imaging device 111.

In embodiments, an imaging device 111 may have one or more attachment elements 141. For example, as illustrated in FIGS. 1C and 1D, multiple attachment elements 141 may be configured for engagement with a transport system, effective to allow transport of the imaging device from one location to another. Such transport may include, for example, transport from a first location (e.g., a location for receiving a sample) to a second location (e.g., a location for imaging a sample) within an automatic sample analysis device or within an automatic sample analysis system.

Accordingly, in embodiments, an internal surface of a chamber of a cuvette comprises an adhesion agent, wherein said adhesion agent is effective to immobilize cells within the chamber. In such imaging devices, a substrate (e.g., an internal surface of a window, or portion of such an internal surface) is coated with an adhesion agent. Such a coating is present on an internal surface of the substrate, where an internal surface is one that forms a wall of an internal chamber or channel of the device. In embodiments, such an adhesion agent may be, e.g., an antibody, an antibody fragment, an antibody mimic, an immunoadhesin, a cell receptor, a ligand, a nucleic acid, a nucleic acid analog, a polypeptide, a polymer, a lectin, a lipid, an oligosaccharide, a polysaccharide, a glue, biotin, avidin, a derivative thereof, and combinations thereof. An adhesion agent, and a coating containing an adhesion agent, is preferably transparent or translucent. In embodiments, a coating containing an adhesion agent is configured or sized (e.g., may be a thin coating) so as to reduce light absorption, light scattering, and other interfering optical effects, to a minimum. In embodiments, a coating containing an adhesion agent may be a dilute coating that is configured to provide sufficient adhesion while providing a minimal amount of light absorption, light scattering, and other interfering optical effects, consistent with effective adhesion.

The substrate is located within a chamber or a channel which contains, or is configured to contain, a fluid biological sample. Adhesion agents immobilize cells in a sample upon contact of the cells with the substrate by binding to the cells. Such binding may be specific binding (e.g., via an antibody) or non-specific binding (e.g., via a resin, glue, or other non-specific agent). Such immobilization aids imaging of the cells by binding cells to the substrate, aiding optical detection by immobilizing the cells to a single plane. Immobilization of the cells to a single plane greatly simplifies the optical requirements, and makes optical measurements (e.g., imaging measurements) easier, more accurate, and more reliable.

A sample may be introduced into a chamber or channel of an imaging device having adhesion agents on substrate via a port that is in fluid communication with the chamber or channel. Such a port may be part of, e.g., may be disposed at one end of, a chamber or channel. More than one port may be in fluid communication with a chamber or channel. In embodiments, a chamber or channel may have two ends, and a port may be located at each of those ends. A fluid sample may be introduced into a chamber or channel via a port, for example, by seating a pipette into the port, effective to make a seal effective to guide the sample into the chamber or channel and to prevent leakage of the sample out of the port during transfer.

A pipet used to fill a chamber or channel may include a vent, effective to allow gas or fluid flow to compensate for any volume changes caused by introduction of the sample into the chamber or channel. Where a chamber or channel is in fluid communication with two ports, gas or fluid previously filling the chamber or channel may flow out of one port when sample is introduced into the chamber or channel via the other port. During filling, or after filling, a sample may be caused to flow in more than one direction within a chamber or channel. Following filling of a chamber or channel with sample, or following multi-directional flow in the chamber or channel, oil may be placed into the port to provide a fluid seal to prevent evaporation of the sample. In embodiments, oil may be placed into both of two ports to provide a fluid seal at each end of a channel or chamber to prevent evaporation of the sample. In embodiments, a pipet may remain engaged with, and sealed to, a port following introduction of sample into a chamber or channel. In embodiments, a pipet may be removed from a port following introduction of sample into a chamber or channel. In embodiments, a cap or lid may be placed over a port, e.g., following filling of a chamber or channel. In embodiments, a cap or lid may be in place over a port prior to filling of a chamber or channel. In embodiments, a pierceable seal (which may be a cap or lid, or may be a thin membrane such as a rubber, plastic, or aluminized plastic sheet) may be in place over a port prior to the filling of a chamber or channel. In embodiments, a pipet may pierce a cap, lid, or seal in place over a port.

Filling a chamber or channel with a sample is effective to place the sample in contact with the substrate. Where the substrate has adhesion agents on its surface, cells in the sample will become attached to the substrate (e.g., the cells will be immobilized on the substrate). The sample will typically be allowed to rest for a period of time in contact with the substrate. Such a period of time may be effective to increase the numbers of cells immobilized on the substrate. Accordingly, a sample introduced into a chamber or channel of an imaging device having adhesion agents on substrate may be induced to flow across the substrate; and will typically be allowed to rest for a period of time in contact with the substrate. In embodiments, the period of time in which the sample is in contact with the substrate includes a period of time in which optical measurements are made.

In embodiments, a sample may be introduced into a chamber or channel, and induced to flow across the substrate in a first direction, and then induced to flow across the substrate in a second direction (e.g., in a direction opposite to the first direction). For example, where a chamber or channel is in fluid communication with two ports, pipets may be sealed to each of the ports, and sample introduced into the chamber or channel via one, or the other, or both ports. Sample introduction by one pipet will induce flow in a first direction, while sample introduction by the other pipet will induce flow in a second direction. In embodiments, where a chamber or channel is in fluid communication with two ports, pipets may be sealed to each of the ports, and sample introduced into the chamber or channel via one of the ports, and air, or fluid introduced via the other port, effective to induce flow in different directions by alternation of flow via one, and then the other, pipet. For example, sample introduction by one pipet will induce flow in a first direction, while air or fluid introduction by the other pipet will induce flow in a second direction.

In further embodiments, a sample may be introduced into a chamber or channel; induced to flow across the substrate in a first direction; induced to flow across the substrate in a second direction; again induced to flow across the substrate in the first direction; and again induced to flow across the substrate in the second direction. In further embodiments, such flow, and reversals of flow direction, is repeated further times. Such flow across the substrate increases the contact between the substrate and the sample, and in particular, increases the likelihood of contact between cells in the sample and the substrate by repeated flow across the substrate. Such increased likelihood of contact between cells in the sample and the substrate increases the likelihood of cells to become attached to the substrate, and increases the number of cells attached to the substrate. Such attachment of cells to the substrate aids imaging of the cells by providing greater numbers of immobilized cells for inspection.

Methods for Imaging Cells Under Microgravity Conditions Using Adhesion Agents

Thus, a method of imaging cells in microgravity includes: contacting a sample with adhesion agents in microgravity, where said adhesion agents are attached to an optically transmissive substrate, effective to attach the cells to the substrate; and imaging the cells.

A further method of imaging cells in microgravity includes: providing an imaging device comprising a chamber having a window with adhesion agents coated thereon; introducing a sample into the chamber in microgravity; contacting the sample with the adhesion agents within the chamber, effective to immobilize the cells in the sample on the window; and imaging the cells.

Further methods of imaging cells in microgravity include filling a chamber or channel with a fluid biological sample in microgravity, said chamber or channel comprising adhesion agents attached to an optically transmissive surface (also termed a substrate), effective to contact said sample with adhesion agents, where said adhesion agents are attached to an optically transmissive substrate, effective to attach the cells to the substrate; and imaging the cells. In embodiments, the sample is allowed to rest in contact with the adhesion agents on the optically transmissive surface for a period of time. Such a period of time may be effective to increase the numbers of cells immobilized on the surface beyond the number of cells immobilized on the surface prior to the period of time.

Further methods of imaging cells in microgravity include filling a chamber or channel with a fluid biological sample in microgravity, said chamber or channel comprising adhesion agents attached to an optically transmissive surface, where the sample is induced to flow across the optically transmissive surface, effective to contact said sample with adhesion agents, where said adhesion agents are attached to an optically transmissive surface, effective to attach the cells to the surface; and imaging the cells. In embodiments, the sample is induced to flow across the optically transmissive surface for a period of time. In embodiments, following a period of time during which the sample is induced to flow across the optically transmissive surface, the sample is then allowed to rest in contact with the adhesion agents on the optically transmissive surface for a period of time.

In embodiments of methods of imaging cells in microgravity, in which the sample is induced to flow across an optically transmissive surface, the sample may be induced to flow across the surface in a first direction, and then induced to flow across the surface in a second direction (e.g., in a direction opposite to the first direction).

In further embodiments of methods of imaging cells in microgravity, a sample may be introduced into a chamber or channel; induced to flow across an optically transmissive surface having adhesion agents (also termed a substrate) in a first direction; induced to flow across the surface in a second direction; again induced to flow across the surface in the first direction; and again induced to flow across the surface in the second direction. In further embodiments of methods of imaging cells in microgravity, such flow, and reversals of flow direction, is repeated further times. Such flow across the surface increases the contact between the surface and the sample, and in particular, increases the likelihood of contact between cells in the sample and the surface by repeated flow across the substrate. Such increased likelihood of contact between cells in the sample and the surface increases the likelihood of cells to become attached to the s surface, and increases the number of cells attached to the surface. Such attachment of cells to the surface aids imaging of the cells by providing greater numbers of immobilized cells for inspection.

In embodiments, the period of time during which the sample is allowed to rest in contact with the adhesion agents on the optically transmissive surface, or the period of time during which the sample is induced to flow across the optically transmissive surface, or both, may be at least about 30 seconds, or at least about one minute, or at least about two minutes, or at least about three minutes, or at least about four minutes, or at least about five minutes, or at least about seven minutes, or at least about nine minutes, or at least about ten minutes, or at least about fifteen minutes, or at least about twenty minutes, or at least about twenty five minutes, or at least about thirty minutes, or at least about forty minutes, or at least about fifty minutes, or at least about one hour, or at least about ninety minutes, or at least about two hours, or at least about three hours, or more.

In embodiments, immobilization of cells by use of adhesion agents may be further performed in conjunction with providing a gel or matrix within the chamber containing the fluid biological sample, further immobilizing cells onto or adjacent a window of a chamber or channel.

Accordingly, imaging of cells in a sample in microgravity may be aided by the use of adhesion agents to coat an inner surface of a window of an imaging device. For example, adhesion agents may be used to immobilize cells on an internal surface of a cuvette, effective to place, and retain, the cells in a position suitable for imaging. Such immobilization aids imaging of the cells. In this way, cells in a fluid sample may be placed in an optimal location for imaging even in the absence of significant gravitational field (e.g., under microgravity conditions).

Imaging Devices for Use with Magnetic Particles

In embodiments, cells in a sample may be attached to magnetic particles, and moved to a desired location (e.g., adjacent, or in contact with, an inner surface of a window of an imaging device). In embodiments, the magnetic particles have targeting moieties which bind cells in the sample; such targeting moieties may include, for example, antibodies, nucleic acids, lectins, biotin, avidin, streptavidin, or other agents which may bind target analytes or cells. In embodiments, targeting moieties which bind cells in the sample for use with magnetic particles include any suitable targeting moiety; for example, in embodiments, such targeting moieties may include any compound or material used as an adhesion agent as discussed above regarding the coating of a substrate.

Targeting moieties useful for attaching magnetic particles to cells in a sample include specific compounds which bind cells. For example, targeting moieties useful for attaching magnetic particles to cells in a sample include antibodies and antibody fragments directed to specific cell markers, particularly cell surface markers. In embodiments, the magnetic particles may include fluorescent molecules; for example, a magnetic particle having an antibody to a particular cell surface marker may be labeled with a fluorescent molecule that will thus be indicative of the particular cell surface marker.

Targeting moieties useful for attaching magnetic particles to cells in a sample include less specific, or non-specific, compounds which bind cells. For example, targeting moieties useful for attaching magnetic particles to cells in a sample may include lectins, and may include cell adhesion molecules, and may include other moieties useful for attaching cells.

In embodiments, a sample may be treated so as to alter cell properties in order to increase the binding of magnetic particles to cells in a sample. In embodiments, a sample may be treated so as to provide binding partners on cells in the sample to enhance attachment of magnetic particles to cells in a sample.

Application of a magnetic field effective to move magnetic particles, e.g., to attract magnetic particles towards the source of the field, is effective to move cells attached to the magnetic particles. In embodiments, application of a magnetic field is effective to move attached cells in a chamber towards a window and thus to aid imaging of the cells.

An imaging device for use with imaging cells attached to magnetic particles is configured for use with magnetic particles. In embodiments, the device has a chamber or channel, one wall of which comprises a window suitable for imaging. In embodiments, the chamber or channel is in fluid communication with a port, or with a plurality of ports. In embodiments, the magnetic particles are present in the chamber or channel prior to introduction of the sample into the chamber or channel. For example, magnetic particles may be placed within a chamber or channel during fabrication of the device. For example, magnetic particles may be placed within a chamber or channel following fabrication of the device; in embodiments, magnetic particles may be attached to a wall of a chamber or channel, where such attachment is reversible (e.g., via soluble linkages, or by drying down of a particle suspension within a chamber or channel). Magnetic particles may be retained in place within a chamber or channel by application of a magnetic field prior to introduction of a sample into the chamber or channel.

In embodiments, the magnetic particles are introduced into the chamber or channel coincident with the introduction of the sample into the chamber or channel. In embodiments, the magnetic particles are introduced into the chamber or channel after introduction of the sample into the chamber or channel. In embodiments, the magnetic particles are introduced into the sample prior to introduction of the sample into the chamber or channel. In embodiments, the magnetic particles are immobilized within the chamber or channel prior to introduction of the sample into the chamber or channel. In embodiments, the magnetic particles are immobilized in or by a water-soluble matrix or adhesive within the chamber or channel prior to introduction of the sample into the chamber or channel; in further embodiments, the water-soluble matrix or adhesive is configured to dissolve upon, or following, contact with a fluid biological sample, effective to release the magnetic particles into the sample. In embodiments, such release the magnetic particles into the sample allows the magnetic particles to contact, and bind to, cells within the fluid biological sample. Following application of a magnetic field to a sample containing magnetic particles bound to cells within the sample, the cells within the sample are drawn, under the influence of the magnetic field, to a desired location. In embodiments, such a desired location is a location suitable for optimal imaging of the cells, e.g., a location on or adjacent to an optically transmissive surface such as a window.

A magnetic field may be applied to, or near, a device. Sources of magnetic fields suitable for use with devices, methods, and systems as disclosed herein include permanent magnets, electromagnets, and any other suitable source. The strength of a magnetic field near to a device may be varied by movement of the source of the magnetic field closer to and away from the device; by reorientation of the source of the magnetic field with respect to the device (e.g., by changing the angle (as measured from a line from the north pole of the source to the south pole of the source) between the magnetic field source and the device); by variation in the current applied to an electromagnet; by inserting or removing a ferromagnetic or paramagnetic material between the source and the device; or by any other means.

Figure 2A:
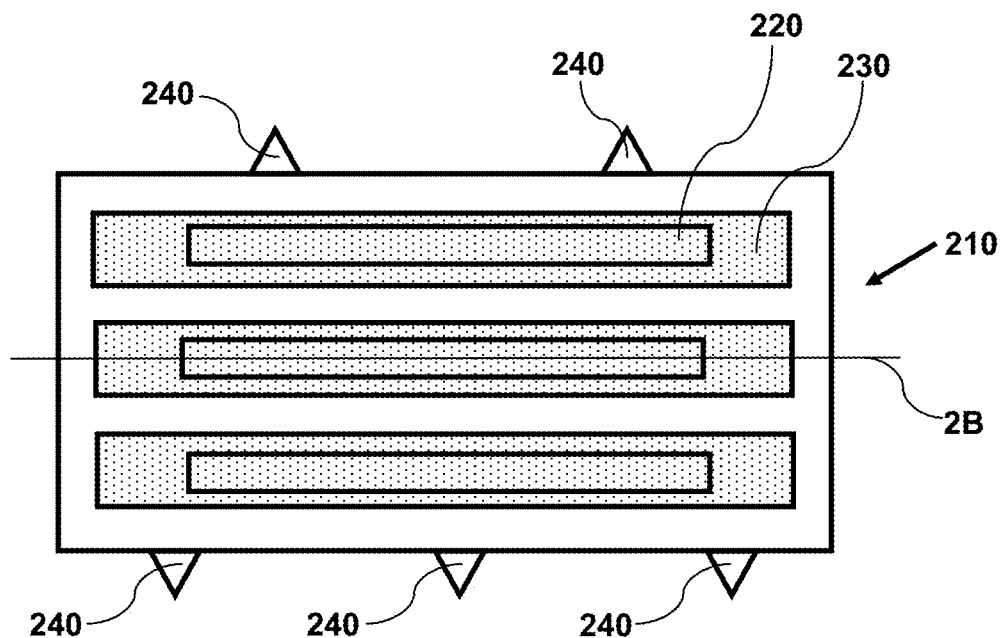
FIG. 2A shows a top view schematic illustration of an imaging device having features as disclosed herein, including a plurality of channels for containing a fluid sample, and a window (in each channel) configured for use with magnetic particles.
Figure 2B:
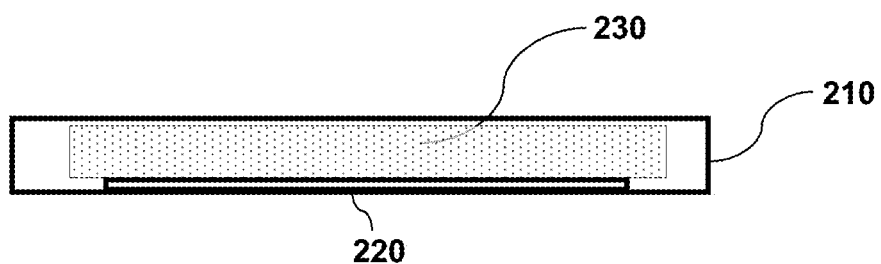
FIG. 2B shows a cross-sectional side view schematic illustration of an imaging device having features as disclosed herein, including a plurality of channels for containing a fluid sample, and a window (in each channel) configured for use with magnetic particles.
Figure 2C:
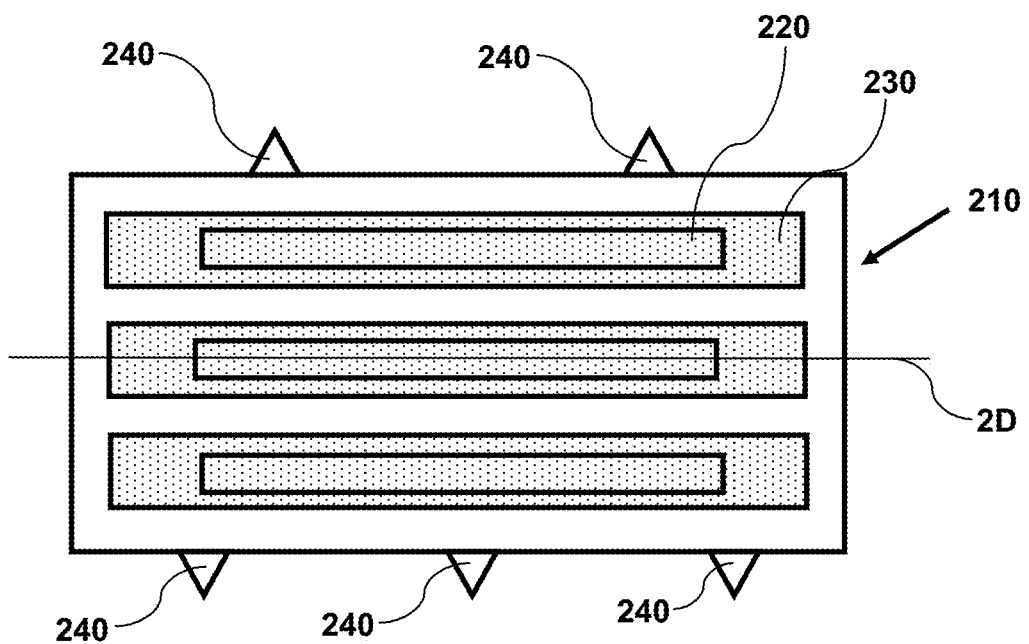
FIG. 2C shows a top view schematic illustration of an imaging device having features as disclosed herein, including a plurality of channels for containing a fluid sample, and a window (in each channel) configured for use with magnetic particles.

FIGS. 2A, 2B, 2C, and 2D provide schematic illustrations of an imaging device 210 having features as disclosed herein, including a plurality of channels 230 for containing a fluid sample, and a window 220 (in each channel) configured for use with magnetic particles. An imaging device 210 may include multiple attachment elements 240, as shown in FIGS. 2A and 2C (attachment elements 240 are not visible in cross-sectional views of the example of an imaging device 210 shown in FIGS. 2A, 2B, 2C, and 2D). Attachment elements 240 are suitable for engagement by a transport system effective to secure the imaging device 210 for transport, or for securing the imaging device 210 in a location suitable for imaging.

The imaging device 210 illustrated in FIGS. 2A, 2B, 2C, and 2D has features as disclosed herein, including a plurality of channels for containing a fluid sample, and a window (in each channel) configured for use with magnetic particles. FIG. 2A (top view) and FIG. 2B (cross-sectional side view, the cross-section taken along the line labeled "2B" in FIG. 2A) illustrate such an imaging device 210 with a sample and magnetic particles within a plurality of channels, prior to application of a magnetic field. The small dots shown within the channels 230, including over the windows 220, represent magnetic particles. The magnetic particles are attached to cells in the sample. As shown in FIGS. 2A and 2B, the magnetic particles are distributed throughout channels 230. The magnetic particles are attached to cells in the sample.

Figure 2D:
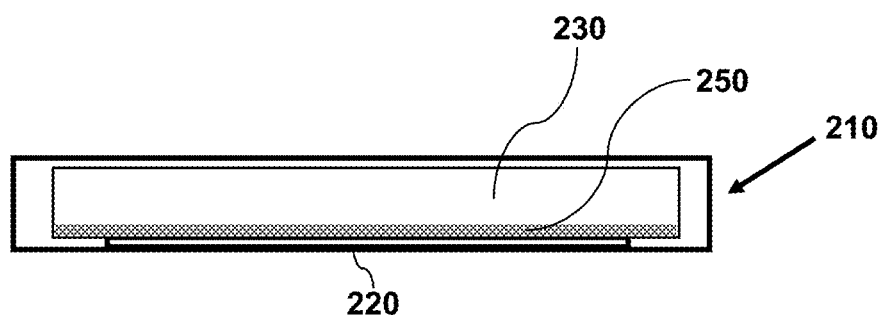
FIG. 2D shows a cross-sectional side view schematic illustration of an imaging device having features as disclosed herein, including a plurality of channels for containing a fluid sample, and a window (in each channel) configured for use with magnetic particles.

FIG. 2C (top view) and FIG. 2D (cross-sectional side view, the cross-section taken along the line labeled "2D" in FIG. 2C) illustrate such imaging device 210 with a sample and magnetic particles within a plurality of channels 230, following application of a magnetic field. Application of a magnetic field is effective to move cells in a fluid sample to the windows 220. The magnetic particles are attached to cells in the sample, and have drawn the cells (which are attached to the magnetic particles) to the windows 220, under the influence of the magnetic field. The movement of the magnetic particles (with attached cells) towards and to the windows 220 is shown in FIG. 2D, which provides a cross-sectional side view of an imaging device 210, window 220, and channel 230, following application of a magnetic field. As illustrated in FIG. 2D, the magnetic particles and attached cells have been drawn to the window 220 by the magnetic field, where they form a thin layer 250. As shown in FIG. 2D, a thin layer 250 of magnetic particles with cells attached lies on the inner surface of the window 220; the rest of the channel 230 is substantially devoid of magnetic particles and cells, illustrated by the lack of small dots shown within channel 230, apart from those shown in layer 250 on the window 220. FIG. 2D illustrates the removal of the magnetic particles and cells from the bulk of the fluid sample within the channel, and the placement of the magnetic particles and attached cells onto the surface of the window 220 under the influence of the magnetic field. In this way, the bulk of the cells in a fluid sample may be placed in an optimal location for imaging even in the absence of significant gravitational field (e.g., under microgravity conditions).

As illustrated in FIG. 2D, the magnetic particles and attached cells have been drawn to the window 220 by the magnetic field, where they form a thin layer 250. As shown in FIG. 2D, a thin layer 250 of magnetic particles with cells attached lies on the inner surface of the window 220; the rest of the channel 230 is substantially devoid of magnetic particles and cells, illustrated by the lack of small dots shown within channel 230, apart from those shown in layer 250 on the window 220.

An imaging device for imaging cells attached to magnetic particles is suitable for use with an external magnet, such as an electromagnet. In embodiments, such an external magnet may be part of an automatic sample analysis device, or an automatic sample analysis system, or other device or system. Thus, in embodiments, an imaging device for imaging cells attached to magnetic particles is suitable for use with an external magnet may be configured for use with such devices and systems comprising a magnet. In embodiments, such a magnet is controllable effective to provide a suitable magnetic field for attracting magnetic particles to a suitable position near to, or on, a window for imaging.

In embodiments, an imaging device for imaging cells attached to magnetic particles comprises a magnet, such as an electromagnet. In embodiments, such a magnet is controllable effective to provide a suitable magnetic field for attracting magnetic particles to a suitable position near to, or on, a window for imaging. In embodiments, such a magnet may be configured to work with an automatic sample analysis device, or an automatic sample analysis system, or other device or system.

Figure 2E:
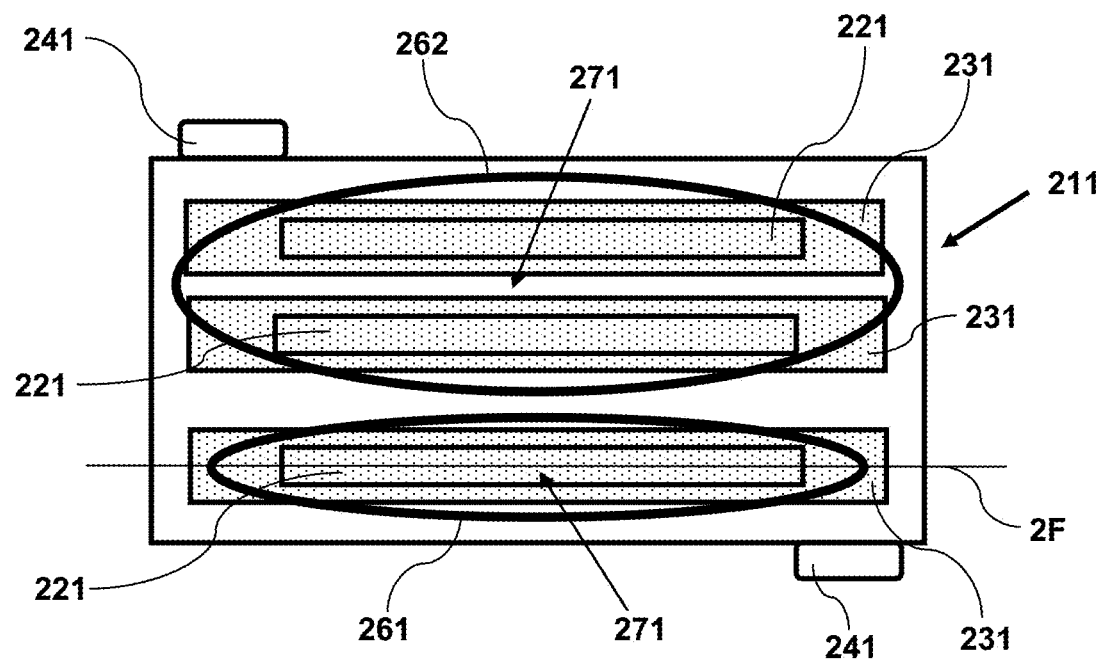
FIG. 2E shows a bottom view of an imaging device having a magnet.
Figure 2F:
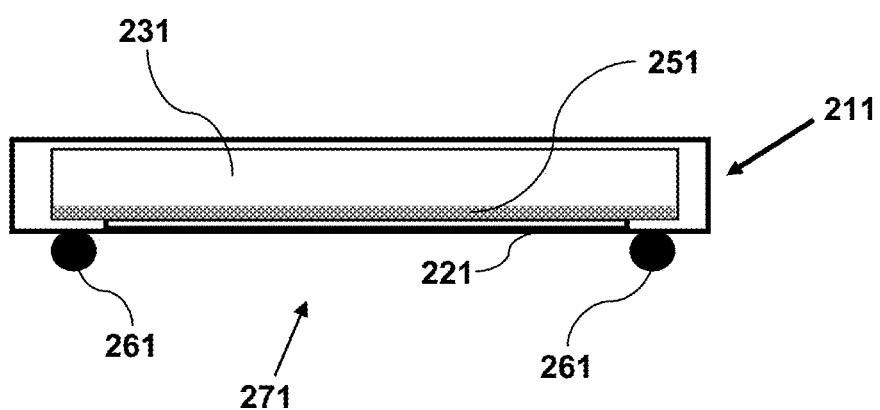
FIG. 2F shows a cross-sectional side view of the imaging device shown in FIG. 2E, where the cross-section is taken along the line 2F shown in FIG. 2E.

For example, as illustrated in FIGS. 2E and 2F, an imaging device 211 may include a magnet 261 or 262. As shown in FIG. 2E, a magnet 261 may be near to a single window 221; in addition, a magnet 262 may be near to multiple windows 221 (two windows as shown in FIG. 2E; or more windows (not shown)). These figures illustrate an imaging device 211 having windows 221 which form portions of the walls of chambers 231, and having a magnet, such as magnet 261 or magnet 262, external to one or more windows 221. The imaging device shown in FIGS. 2E and 2F has attachment elements 241 for moving the device, and for securing the device in a location for imaging and for other actions and operations. As shown in the bottom view shown in FIG. 2F, a magnet 261 may be disposed on an external face of window 221. The magnet 261 shown in FIG. 2F has the annular shape defining an opening 271 radially interior to the solid portions of magnets 261 and 262. Such an opening 271 within an annular-shaped magnet 261 or 262 allows for imaging with the magnet in position. It will be understood that other shapes and openings, or multiple magnets separated from each other by gaps, or other configurations will also allow for imaging with the magnet or magnets in position. A magnetic field provided by a magnet 261 or 262 is effective to move magnetic particles (including magnetic particles with cells attached) within a chamber 231 to suitable positions for imaging, such as to positions on or near to an inner surface of a window 221. An electromagnet may be activated to provide a magnetic field by providing current flow within conductors in the electromagnet, and may be inactivated upon cessation of the current flow. The magnetic field of an electromagnet may be modulated by varying the current flow within conductors in the electromagnet. Positioning of permanent or other magnets, including electromagnets, may also be used to initiate, modulate, and eliminate a magnetic field applied to a chamber 221. As shown in the cross-sectional side view shown in FIG. 2F, magnetic particles (with attached cells) in a sample within chamber 231 are drawn onto and near to a window 221 by operation of the magnet 261 or 262 to form a coating 251 on or near window 221. Cells in such a coating are in suitable positions for imaging.

In embodiments, a chamber or channel configured for use with, or containing, magnetic beads that may bind cells in a sample and draw such cells to a region near a window under the influence of a magnetic field, where such a region is suitable or optimal for imaging, may also include an adhesion agent on an inner surface of the chamber (e.g., on an optically transmissive surface of a window). In embodiments, the position of cells in a fluid biological sample may be maintained by increasing the viscosity of a fluid biological sample; such an increase in viscosity may be accomplished, for example, by providing, or forming, a gel or hydrogel within the chamber, e.g., within the fluid biological sample in the chamber. Increasing the viscosity of a fluid biological sample, or portion thereof, may include forming or providing a gel, such as a hydrogel, within or around the sample. In embodiments, both an adhesion agent and increased viscosity may be used to maintain the position of cells in a sample on or near to a window for imaging.

Methods of Imaging Cells in Microgravity Using Magnetic Particles

Applicant discloses methods in which cells in a fluid biological sample are contacted with, and bound by, magnetic particles in order to enhance imaging of the cells in microgravity. In embodiments of these methods, application of a magnetic field to a sample containing magnetic particles bound to cells within the sample is effective to move such bound cells to a desired location. In embodiments, such a desired location is a location suitable for optimal imaging of the cells, e.g., a location on or adjacent to an optically transmissive surface such as a window.

Accordingly, a method of imaging cells in microgravity includes: contacting a sample with magnetic particles, effective to attach the magnetic particles to cells in the sample; applying a magnetic field effective to move the cells; and imaging the cells. In embodiments, application of the magnetic field is effective to move the cells to a location that is suitable, or that is optimal, for imaging the cells.

A further method of imaging cells in microgravity includes: providing an imaging device comprising a chamber having a window; introducing a sample into the chamber in microgravity; contacting the sample with magnetic particles within the chamber, effective to attach the magnetic particles to cells in the sample; applying a magnetic field effective to move the cells to the window; and imaging the cells. In embodiments, application of the magnetic field is effective to move the cells to a location that is suitable, or that is optimal, for imaging the cells.

In embodiments of the methods of imaging cells in microgravity, magnetic particles may be placed within a chamber or channel prior to the introduction of a fluid biological sample into the device. In embodiments of the methods of imaging cells in microgravity, magnetic particles may be placed within a chamber or channel at the same time as time of introduction of a fluid biological sample into the device. In embodiments of the methods of imaging cells in microgravity, magnetic particles may be placed within a chamber or channel following the introduction of a fluid biological sample into the device.

In embodiments of the methods of imaging cells in microgravity in which magnetic particles are placed within a chamber or channel prior to the introduction of a fluid biological sample into the device, the magnetic particles may be immobilized within the chamber or channel. In embodiments of the methods of imaging cells in microgravity in which magnetic particles are immobilized within a chamber or channel prior to the introduction of a fluid biological sample into the device, such immobilization may be accomplished by a water-soluble matrix or adhesive; such a water-soluble matrix or adhesive may dissolve, or become ineffective to immobilize the magnetic particles, upon or soon after contact with the fluid biological sample.

Accordingly, a method of imaging cells in microgravity includes: providing a fluid biological sample within a chamber containing magnetic particles immobilized in or by a water-soluble matrix or adhesive; contacting the water-soluble matrix or adhesive with the fluid biological sample, effective to dissolve or inactivate the water-soluble matrix or adhesive, thereby releasing the magnetic particles, effective to contact cells within the sample with said magnetic particles, effective to attach the magnetic particles to cells in the sample; applying a magnetic field effective to move the cells; and imaging the cells. In embodiments, application of the magnetic field is effective to move the cells to a location that is suitable, or that is optimal, for imaging the cells.

A further method of imaging cells in microgravity includes: providing an imaging device comprising a chamber having a window, and comprising magnetic particles immobilized in or by a water-soluble matrix or adhesive within the chamber; introducing a fluid biological sample into the chamber in microgravity; contacting the water-soluble matrix or adhesive with the fluid biological sample, effective to dissolve or inactivate the water-soluble matrix or adhesive, thereby releasing the magnetic particles, effective to contact cells within the sample with said magnetic particles, effective to attach the magnetic particles to cells in the sample; applying a magnetic field effective to move the cells to the window; and imaging the cells. In embodiments, application of the magnetic field is effective to move the cells to a location that is suitable, or that is optimal, for imaging the cells. In embodiments, the cells may be immobilized following movement to a desired location under the influence of a magnetic field. In embodiments, such immobilization following movement of cells under the influence of a magnetic field may comprise contacting the cells with adhesion agents, where the adhesion agents are localized on an inner surface of the window. In embodiments, such immobilization may comprise providing a gel or matrix within the chamber containing the fluid biological sample, following movement of cells under the influence of a magnetic field onto or adjacent the window.

Accordingly, imaging of cells in a sample in microgravity may be aided by the use of magnetic particles. For example, magnetic particles may be used to move cells to an internal surface of a cuvette, effective to place, and immobilize, the cells in a position suitable for imaging. Such immobilization aids imaging of the cells.

Narrow Chambers and Channels

In embodiments, a chamber or channel of transportable device for imaging (e.g., a cuvette) has dimensions of the order of the dimensions of a cell in a fluid biological sample. Such dimensions act to constrain cells in a sample to within a small region adjacent the window of the cuvette, which aids in imaging of the cells. In a typical configuration where the imaging optics view the sample via a window, with the imaging optics external to the window, it is in general the case that the closer the cells to the window the better the imaging. Where the biological sample is held in a chamber or channel adjacent a window, and where the height of the chamber or channel is defined as the perpendicular distance between the inner surface of the window and the opposite wall (parallel to the plane of the window), the height may be determined by the optical properties of a detection system (e.g., lenses, filters, and other optical elements) used to image the biological sample. In embodiments, an upper limit for the height of such a chamber, where the height is measured by distance from the inner surface of the window, may be determined by the optical properties of a detection system (e.g., lenses, filters, and other optical elements) used to image the biological sample.

That is, the height will typically be determined by the depth of field of the imaging system, so that no cell or object of interest in the sample may be farther from the window than can be suitably imaged by the detection system. Typically, the detection system will be configured for a single focal length or focal plane, so that cells to be imaged must be placed within a narrow range of distance from the window. However, in embodiments, the detection system may be configured to change its focus, so that the height may be greater than for configurations in which the detection system has a single distance than can be suitably imaged by the detection system. In embodiments, a chamber or channel adjacent a window may have a height of between about 5 µm to about 50 µm. In embodiments, a chamber or channel adjacent a window may have a height of no less than about 5 µm, or no less than about 10 µm, or no less than about 15 µm, or no less than about 20 µm. In embodiments, a chamber or channel adjacent a window may have a height of between about 10 µm to about 40 µm, or between about 10 µm to about 30 µm, or between about 10 µm to about 20 µm. Where the optical properties of the detection system allow it (e.g., suitable focal length, or resolution, or light intensity, or other optical parameter) a chamber or channel adjacent a window may have a height of up to about 100 μm, or 200 μm, or 300 μm, or 400 μm, or 500 μm, or more. Examples of embodiments in which the optical properties of the detection system allow a height of more than about 50 μm include those in which the detection system has an adjustable focal length, or is otherwise configured to have multiple, or variable, focal lengths.

In embodiments, an imaging device has one or more chambers or channels configured to constrain cells to a narrow range of distances adjacent a window. In embodiments, chambers or channels configured to constrain cells to a narrow range of distances adjacent a window have the same height along the length of the chamber or channel. In embodiments, chambers or channels configured to constrain cells to a narrow range of distances adjacent a window comprise a portion adjacent a window having dimensions different than the dimensions of other portions of the chamber or channel; for example, a chamber or channel may have a constriction, or narrowing, adjacent the window. In embodiments, chambers or channels configured to constrain cells to a narrow range of distances adjacent a window comprise a plurality of portions having a constriction, or narrowing (e.g., having decreased height as compared to other portions of the chamber or channel), some or all of which narrowings are adjacent a window. The narrowings reduce the height of the channels (where the height of the channels is measured in a direction substantially parallel to the direction of imaging, and substantially perpendicular to the direction of flow within the channel).

In embodiments, a chamber or channel having a height, or other dimension, configured to constrain cells in a sample to a region near a window, where such a region is suitable or optimal for imaging, may also include an adhesion agent on an inner surface of the chamber (e.g., on an optically transmissive surface of a window). In embodiments, a chamber or channel having a configuration in which a height, or other dimension, is of a size effective to constrain cells in a sample to a region near a window, where such a region is suitable or optimal for imaging, may also include an adhesion agent on an inner surface of the chamber (e.g., on an optically transmissive surface of a window). In embodiments, the position of cells in a fluid biological sample may be maintained by increasing the viscosity of a fluid biological sample; such an increase in viscosity may be accomplished, for example, by providing, or forming, a gel or hydrogel within the chamber, e.g., within the fluid biological sample in the chamber. Increasing the viscosity of a fluid biological sample, or portion thereof, may include forming or providing a gel, such as a hydrogel, within or around the sample. In embodiments, both an adhesion agent and increased viscosity may be used to maintain the position of cells in a sample on or near to a window for imaging.

Figure 3A:
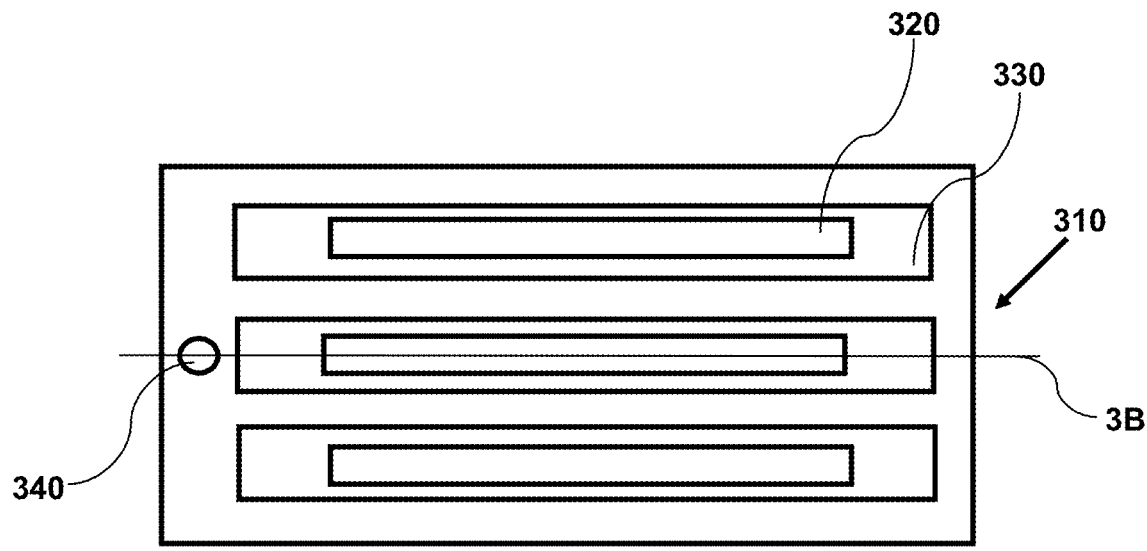
FIG. 3A provides a top view schematic illustration of an imaging device with a sample within a plurality of channels, where the channels are narrow. The narrow channel forces cells in the sample into a position near to the window.
Figure 3B:
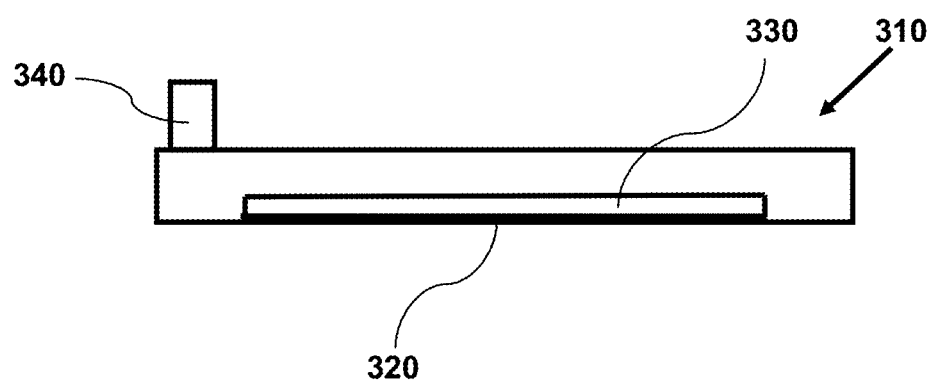
FIG. 3B provides a cross-sectional side view schematic illustration of an imaging device with a sample within a plurality of channels, where the channels are narrow. The narrow channel forces cells in the sample into a position near to the window. The cross-section is taken along the line 3B shown in FIG. 3A.

FIG. 3A provides a top view schematic illustration of an imaging device 310 with windows 320, configured to hold a sample within a plurality of chambers (shown as channels 330) having windows 320. An imaging device 310 also has an attachment element 340 suitable for engagement by a transport system effective to secure the imaging device 310 for transport, or for securing the imaging device 310 in a location suitable for imaging. The channels 320 of imaging devices 310 are sufficiently narrow so as to constrain cells within a fluid sample to be in locations suitable for imaging; thus, all cells within a narrow channel 330 may be imaged through a window 320. FIG. 3B provides a cross-sectional side view schematic illustration of an imaging device 310 with a sample within a plurality of channels 330 with windows 320, illustrating in side view the narrow channel 330 adjacent a window 320. Cells in a fluid sample within the narrow region 360 are constrained to be in positions near to the window 320, and thus are constrained to be in positions suitable for imaging. Thus, all, or mostly all, cells within a fluid sample within such a narrow channel 330 will be in focus when imaged by imaging apparatus applied to the imaging device 310.

In embodiments, the height of a narrow channel 330 is less than about 100 micrometers (μm); in embodiments, the height of a narrow channel 330 is less than about 75 μm, and in embodiments, the height of a narrow channel 330 is less than about 50 μm. In embodiments, the height of a narrow channel 330 is between about 8 μm and about 100 μm. In embodiments, the height of a narrow channel 330 is between about 10 μm and about 75 μm. In embodiments, the height of a narrow channel 330 is between about 15 μm and about 50 μm.

Figure 3C:
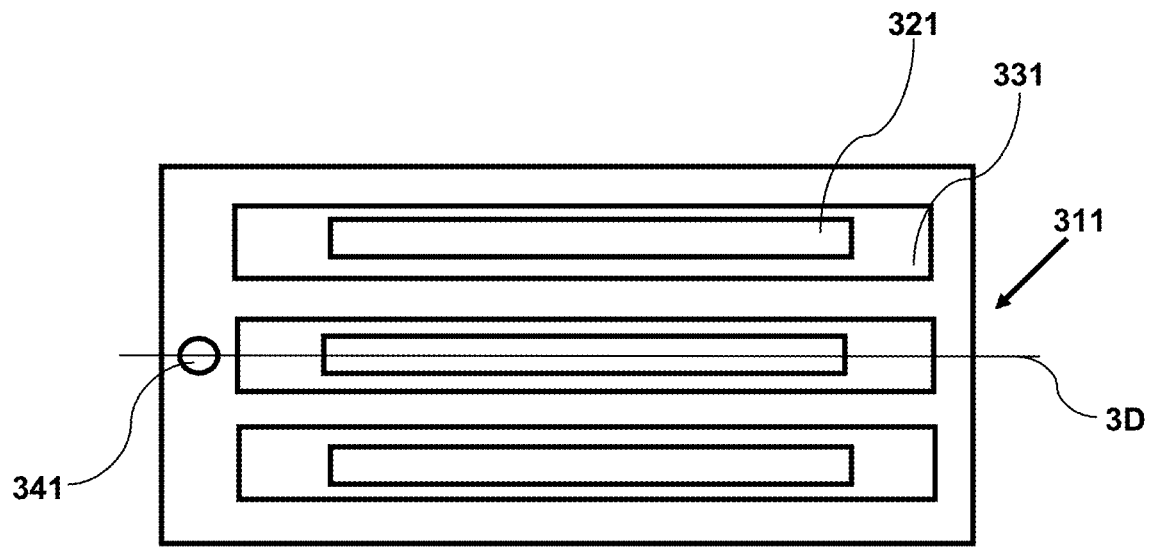
FIG. 3C provides a top view schematic illustration of an imaging device with a sample within a plurality of channels, where the channels have a narrow region adjacent a window. The narrow region forces cells in the sample into a position near to the window.
Figure 3D:
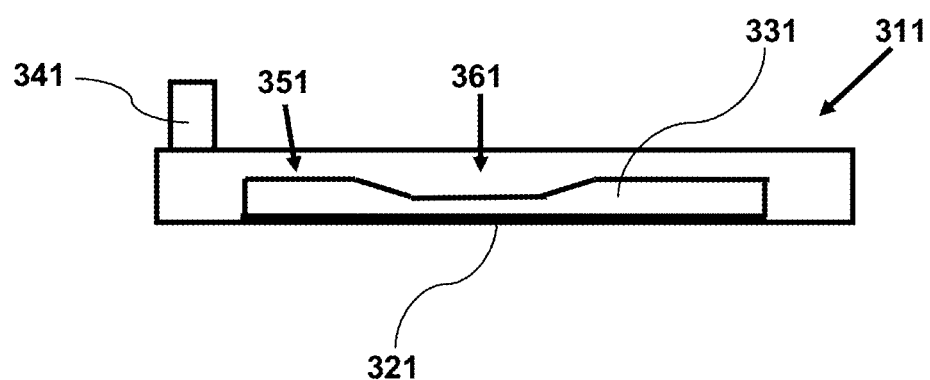
FIG. 3D provides a cross-sectional side view schematic illustration of an imaging device with a sample within a plurality of channels, where the channels have a narrow region adjacent a window. The narrow region forces cells in the sample into a position near to the window. The cross-section is taken along the line 3D shown in FIG. 3C.

FIG. 3C provides a top view schematic illustration of an imaging device 311 with windows 321, configured to hold a sample within a plurality of channels 331 having windows 321. An imaging device 311 also has an attachment element 341 suitable for engagement by a transport system effective to secure the imaging device 311 for transport, or for securing the imaging device 310 in a location suitable for imaging. The channels 321 of imaging devices 311 have wide regions 351 and narrow regions 361. FIG. 3B provides a cross-sectional side view schematic illustration of an imaging device 311 with a sample within a plurality of channels 331 with windows 321, illustrating a narrow region 361 adjacent a window 321, and wide regions 351 with portions nearer to, and portions farther from, the surface of the window 321. Cells in a fluid sample within the narrow region 360 are constrained to be in positions near to the window 321, and thus are constrained to be in positions suitable for imaging. The narrow region 361 forces cells in the sample into a position near to the window 321, and, lacking room in positions less favorable for imaging, constrains cells within a sample to be within region suitable for imaging. Thus, all, or mostly all, cells within a fluid sample within such a narrow region 361 will be in focus when imaged by imaging apparatus applied to the imaging device 311. In contrast, only some cells within a fluid sample within a wide region 350 will be in focus when imaged by imaging apparatus applied to the imaging device 311 (i.e., those cells within a wide region 351 that are disposed near to the surface of window 321 will be in focus and suitable for imaging; other cells within that region 351, farther from the surface of window 321, will not be in focus and will not be suitable for imaging). In embodiments, imaging of cells in a fluid sample is mainly, or is only, performed on cells within narrow region 361. In embodiments, imaging of cells in a fluid sample is not performed on cells within a wide region 351. In embodiments, imaging of cells in a fluid sample is mainly, or is only, performed through a portion of window 321 that is adjacent to narrow region 361. In embodiments, imaging of cells in a fluid sample is not performed through a portion of window 321 that is adjacent to a wide region 351.

In embodiments, the height of a narrow region 361 is less than about 100 micrometers (μm); in embodiments, the height of a narrow region 361 is less than about 75 μm, and in embodiments, the height of a narrow region 361 is less than about 50 μm. In embodiments, the height of a narrow region 361 is between about 8 μm and about 100 μm. In embodiments, the height of a narrow region 361 is between about 10 µm and about 75 µm. In embodiments, the height of a narrow region 361 is between about 15 µm and about 50 µm.

In embodiments, the height of a chamber or a channel of a cuvette, or of a portion of a chamber or channel, may be alterable. For example, a chamber or channel may be configured so that its height may be a first height when a fluid biological sample is introduced, and may be configured to decrease its height to a second, lesser, height following introduction of the sample. Such a reduction in height is effective to force cells in the sample that are opposite a window to positions closer to the window. In embodiments where the height of a chamber or channel may be altered, a wall or portion thereof may be made of a porous material effective that fluid may exit the chamber or channel, but cells may not exit the chamber or channel. In embodiments, the porous material may be a membrane, or filter, or mesh, or grid, or a material having apertures, or other material. In embodiments, a chamber wall or portion thereof may comprise a compressible material. In embodiments in which a chamber wall or portion thereof comprises a compressible material, that wall or portion thereof may serve as a gasket. In embodiments, a wall or portion thereof may be made of a porous material and a chamber wall or portion thereof may comprise a compressible material. In embodiments in which the height of a chamber or a channel, or portion thereof, of a cuvette, may be alterable, decreasing that height may be effective to constrain cells to a narrow range of distances adjacent a window.

Figure 4A:
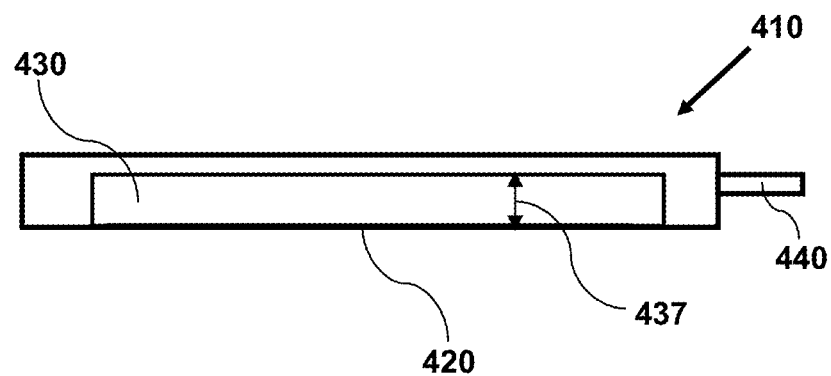
FIG. 4A provides a cross-sectional side view illustration of an imaging device having a reconfigurable channel. The channel in 4A is shown in a first configuration having a wide height. As shown in the accompanying FIG. 4B, the channel may be reconfigured so as to have a narrow height, constraining cells to regions adjacent a window.
Figure 4B:
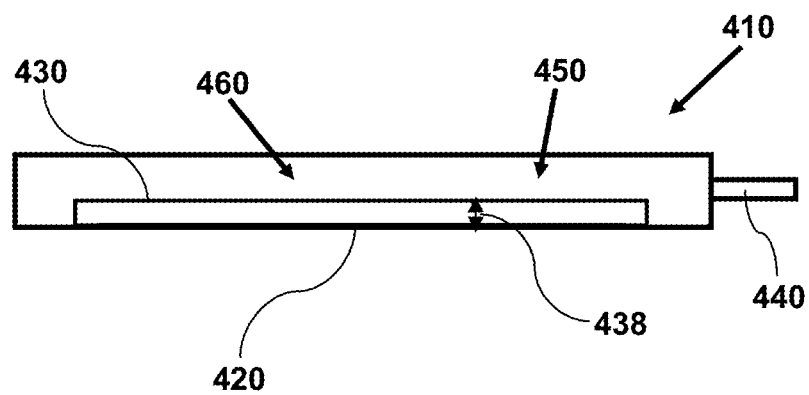
FIG. 4B provides a cross-sectional side view illustrating an imaging device as in FIG. 4A with a sample within a channel, showing the channel configuration subsequent to its reconfiguration, providing a channel having a narrow height. A fluid sample having cells may be held within the channel. The narrow height forces cells in the sample into a position near to the window. The channel may be reconfigured to its narrow, second configuration at any time prior to, during, or following introduction of a fluid sample into the channel.

FIG. 4A provides a cross-sectional side view illustration of an imaging device 410 with a window 420 and having a reconfigurable chamber, shown as channel 430 in FIGS. 4A and 4B. A reconfigurable channel 430 has a first configuration, having a wide first height 437, and a second configuration, having a narrow second height 438. An imaging device 410 also has an attachment element 440. An imaging device 410 also has an attachment element 440 suitable for engagement by a transport system effective to secure the imaging device 410 for transport, or for securing the imaging device 410 in a location suitable for imaging. A fluid sample having cells may be held within the channel 430. A channel 430 of an imaging device 410 as shown in FIGS. 4A and 4B has a first height 437 (shown in FIG. 4A) that is greater than the second height 438 (shown in FIG. 4B). Thus, a channel 430 of an imaging device 410 as shown in FIGS. 4A and 4B may be reconfigured to have a narrow height 438 within channel 430 adjacent window 420 (shown in FIG. 4B). Thus, at a time when a sample is introduced into a channel 430 of the imaging device 410, the channel 430 has a wide height 437 along its entire length (shown in FIG. 4A). As shown in the FIG. 4B, the channel 430 may be reconfigured (e.g., at a time subsequent to the introduction of a sample into the channel 430) so as to have a narrow height 438 adjacent a window 420. Thus, reconfiguration of channel 430 results in narrower channel 430, having a narrow height 438. The narrow height 438 forces cells in the sample into a position near to the window 420; such a position is suitable for imaging cells within a fluid sample within a channel 430 in an imaging device 410.

Cells in a fluid sample within the channel 430 in its second configuration having narrow height 438 are constrained to be in positions near to the window 420, and thus are constrained to be in positions suitable for imaging. The narrow height 438 forces cells in the sample into a position near to the window 420, and, lacking room in positions less favorable for imaging, constrains cells within a sample to be within region suitable for imaging. Thus, all, or mostly all, cells within a fluid sample within a channel 430 in its second configuration having narrow height 438 will be in focus when imaged by imaging apparatus applied to the imaging device 410.

In embodiments, narrow height 438 of a channel 430 in its narrow (second) configuration is less than about 100 micrometers (µm); in embodiments, narrow height 438 of a channel 430 in its narrow (second) configuration is less than about 75 µm, and in embodiments, narrow height 438 of a channel 430 in its narrow (second) configuration is less than about 50 µm. In embodiments, the narrow height 438 of a channel 430 in its narrow (second) configuration is between about 8 µm and about 100 µm. In embodiments, the narrow height 438 of a channel 430 in its narrow (second) configuration is between about 10 µm and about 75 µm. In embodiments, the narrow height 438 of a channel 430 in its narrow (second) configuration is between about 15 µm and about 50 µm.

Figure 4C:
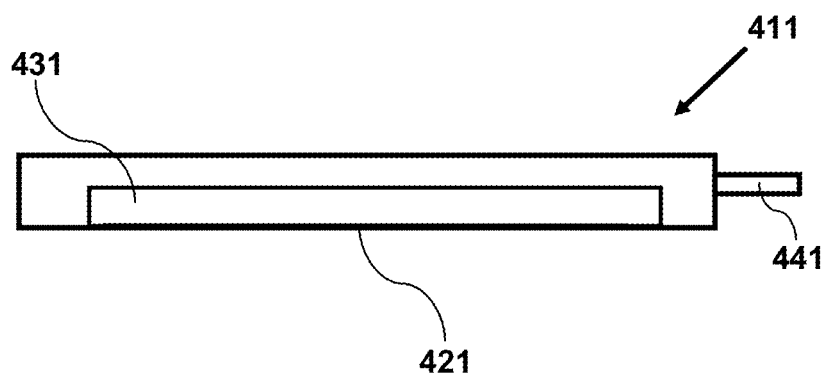
FIG. 4C provides a cross-sectional side view illustration of an imaging device having a reconfigurable channel. The channel initially does not have a narrow region adjacent a window. As shown in the accompanying figure, the channel may be reconfigured so as to have a narrow region adjacent a window.
Figure 4D:
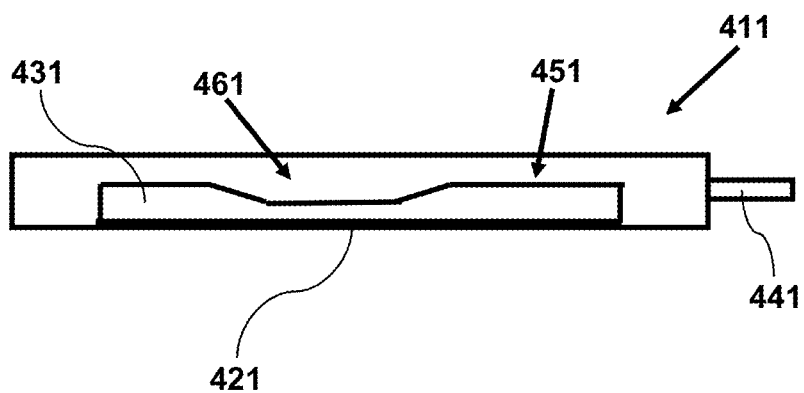
FIG. 4D provides a cross-sectional side view illustrating an imaging device as in FIG. 4C with a sample within a channel, showing the channel configuration subsequent to its reconfiguration, providing a channel having a narrow region adjacent a window. A fluid sample having cells may be held within the channel. The narrow region forces cells in the sample into a position near to the window. The channel may be reconfigured prior to, during, or following introduction of a fluid sample into the channel.

FIG. 4C provides a cross-sectional side view illustration of an imaging device 411 with a window 421 and having a reconfigurable channel 431. An imaging device 411 also has an attachment element 441. An imaging device 411 also has an attachment element 441 suitable for engagement by a transport system effective to secure the imaging device 411 for transport, or for securing the imaging device 411 in a location suitable for imaging. A fluid sample having cells may be held within the channel 431. A channel 431 of an imaging device 411 as shown in FIGS. 4C and 4D has a region, or regions 451, where the height of the regions 451 is an original height. A channel 431 of an imaging device 411 as shown in FIGS. 4C and 4D may be reconfigured to have a narrow region 461 within channel 431 adjacent window 421 (shown in FIG. 4D). Thus, as shown in FIG. 4C, at a time when a sample is introduced into a channel 431 of the imaging device 411, the channel 431 has an original height along its entire length. As shown in the FIG. 4D, the channel 431 may be reconfigured (e.g., at a time subsequent to the introduction of a sample into the channel 431) so as to have a narrow region 461 adjacent a window, and to have other regions 451 having greater height than the narrow region 461. Regions 451 may have heights that are the same as the original height of the channel 431 prior to reconfiguration of region 461. Thus, while reconfiguration of channel 431 results in narrow region 461, regions 451 are not reconfigured, and remain their original height even after region 461 is reconfigured to have a lesser height to become narrow region 461. The narrow region 461 forces cells in the sample into a position near to the window 421.

Cells in a fluid sample within the narrow region 461 are constrained to be in positions near to the window 421, and thus are constrained to be in positions suitable for imaging. The narrow region 461 forces cells in the sample into a position near to the window 421, and, lacking room in positions less favorable for imaging, constrains cells within a sample to be within region suitable for imaging. Thus, all, or mostly all, cells within a fluid sample within such a narrow region 461 will be in focus when imaged by imaging apparatus applied to the imaging device 411. In contrast, only some cells within a fluid sample within a wide region 451 will be in focus when imaged by imaging apparatus applied to the imaging device 411 (i.e., those cells within a wide region 451 that are disposed near to the surface of window 421 will be in focus and suitable for imaging; other cells within that region 450, farther from the surface of window 421, will not be in focus and will not be suitable for imaging). In embodiments, imaging of cells in a fluid sample is mainly, or is only, performed on cells within narrow region 461. In embodiments, imaging of cells in a fluid sample is not performed on cells within a wide region 451. In embodiments, imaging of cells in a fluid sample is mainly, or is only, performed through a portion of window 421 that is adjacent to narrow region 461. In embodiments, imaging of cells in a fluid sample is not performed through a portion of window 421 that is adjacent to a wide region 451.

In embodiments, the height of a narrow region 461 is less than about 100 micrometers (μm); in embodiments, the height of a narrow region 461 is less than about 75 μm, and in embodiments, the height of a narrow region 461 is less than about 50 μm. In embodiments, the height of a narrow region 461 is between about 8 μm and about 100 μm. In embodiments, the height of a narrow region 461 is between about 10 μm and about 75 μm. In embodiments, the height of a narrow region 461 is between about 15 μm and about 50 μm.

In embodiments, the height of a wide region 451 is more than about 50 micrometers (μm); in embodiments, the height of a wide region 451 is more than about 75 μm, and in embodiments, the height of a wide region 451 is less than about 100 μm.

Flow of a sample into a chamber or channel having a narrow region adjacent a window may be aided by providing a hydrophilic surface or surfaces within the chamber or channel; for example, glass may provide such a hydrophilic surface. Thus, in embodiments, a window may be made of glass. In further embodiments, a hydrophilic surface may be provided by treatment of the surface (e.g., a plastic) to provide a more hydrophilic (e.g., charged) surface. In further embodiments, a surface of a chamber or channel may be coated in order to increase its hydrophilicity. In embodiments, surfactants or other agents may be added to the sample to aid its flow into a narrow region of a chamber or channel.

A sample may be induced to flow within a narrow region, for example, by application of fluid pressure. For example, where a chamber or channel is in fluid communication with a port, and the chamber or channel has a vent, a pipet sealed to the port may introduce the sample by applying pressure, as needed, to cause the sample to flow into the chamber or channel and into (and through, if desired) the narrow region. Cells may be held in place on or near a window by an adhesion agent during or following such flow.

Where a chamber or channel is in fluid communication with two ports, pipets may be sealed to each of the ports, and sample introduced into the chamber or channel via a first port by applying pressure as needed. Suction may be applied to the chamber or channel by the second pipet, as needed, effective to induce flow of the sample into (and through, if desired) the narrow region. In embodiments, little or no pressure may be applied via the first port, while suction is applied to the chamber or channel by the second pipet, effective to induce flow of the sample into (and through, if desired) the narrow region.

Methods of Imaging Cells in Microgravity in Imaging Devices with Narrow Regions

Accordingly, Applicant discloses methods for imaging cells in a fluid biological sample in microgravity, in which cells of such a fluid biological sample are mechanically constrained to a desired location, or to desired locations, within an imaging device. In embodiments, a desired location is a location suitable for optimal imaging of the cells, e.g., a location on or adjacent to an optically transmissive surface (also termed an optically transmissive substrate; a surface; or a substrate) such as a window. In embodiments, a desired location may be, for example, a location adjacent to, or in contact with, an inner surface of a window of an imaging device.

Thus, a method of imaging cells in microgravity includes: placing a sample within a chamber in microgravity, where said chamber has a narrow region adjacent an optically transmissive substrate, wherein said narrow region is configured to constrain cells in said sample to positions near to the substrate; and imaging the cells.

A further method of imaging cells in microgravity includes: providing an imaging device comprising a chamber having a window and narrow region configured to constrain cells in chamber to positions near to the window; introducing a sample into the chamber in microgravity, effective to position cells in the sample near to the window; and imaging the cells.

In such embodiments, providing a window adjacent a narrow region effective to constrain cells in a sample to within a narrow range of distances adjacent the window aids imaging of the cells. In embodiments, such cells may be maintained in position by an adhesion agent coating the window, by increasing viscosity of the fluid, or both.

A further method of imaging cells in microgravity includes: placing a sample within a chamber in microgravity, wherein said chamber comprises a window, said chamber having a chamber height adjacent said window; decreasing said chamber height following introduction of the sample into the chamber, effective to provide a narrow region adjacent the window, wherein said narrow region is configured to constrain cells in said sample to positions near to the substrate; and imaging the cells. In embodiments, such cells may be maintained in position by an adhesion agent coating the window, by increasing viscosity of the fluid, or both.

In such embodiments, decreasing the height of a chamber or channel is effective to constrain cells in a sample to within a narrow range of distances adjacent a window. Such positioning of the cells aids imaging of the cells. In this way, cells in a fluid sample may be placed in an optimal location for imaging even in the absence of significant gravitational field (e.g., under microgravity conditions).

Positioning of cells in a fluid biological sample may be maintained by increasing the viscosity of a fluid biological sample; such an increase in viscosity may be accomplished, for example, by providing, or forming, a gel or hydrogel within the chamber, e.g., within the fluid biological sample in the chamber. Increasing the viscosity of a fluid biological sample, or portion thereof, may include forming or providing a gel, such as a hydrogel, within or around the sample. Many materials, including materials compatible with, and often found in, biological samples, may be used to form gels and hydrogels. Suitable materials for forming gels and hydrogels include polymers (e.g., polyethylene glycols (PEG)), block co-polymers (e.g., ethylene oxides and propylene oxide (Pluronics®)), alginate, agarose, dextran, gelatin, gellan and gellan gum, pectin, silk fibroin, inorganic phosphates, heparin, hyaluronic acid, collagen, chitosan, cellulose and hydroxypropyl methylcellulose, fibrin, fibrinogen, and other compounds and materials. For example, suitable gels or hydrogels may include polyethylene glycol polymers and derivatives, including polyethylene glycol diacrylate ((PEGDA), also known as polyethylene oxide (PEO)). Such polymers may be crosslinked to form transparent gels and hydrogels effective to immobilize (or substantially immobilize for periods sufficient for observation or imaging) cells or particles within a fluid biological sample. Crosslinking may be accomplished by chemical means (e.g., mixing pyrrolidinone-containing compounds with maleimide-containing compounds, or other reactive pairs of compounds; contacting a fluid biological sample with aldehyde-containing reagents or other reagents; and other means); by photochemical means (e.g., by illumination of a fluid biological sample following contacting the sample with reagents containing a photoinitiator (such as, e.g., aromatic carbonyl-containing ketone photoinitiators, including 2-hydroxy-1-[4-(2-hydroxyethoxy) phenyl]-2-methyl-1-propanone (Ciba 12959), which initiates polymerization upon exposure of the sample/photoinitiator mixture to 365 nm ultraviolet light); other photoinitiators include, for example, acylphosphine oxide photoinitiators, camphorquinones, and others); by heating; or by other means. Hydrogel properties like gelation time, elastic modulus, transparency, can all be modulated by varying initiator or cross-linker concentrations, macromer length, macromer weight percent, degree of acrylate modification (for acrylate-containing polymers and block co-polymers), illumination intensity and duration (for photoinitiated reactions), heat, and other parameters. In this way, cells in a fluid sample may be maintained in an optimal location for imaging even in the absence of significant gravitational field (e.g., under microgravity conditions).

Imaging Devices for Use with Centrifugation

In embodiments, cells in a sample may be directed to a window under the influence of centrifugation. In such embodiments, a cuvette may be used, the cuvette having a chamber having an optically transmissive surface (e.g., a window) and an upper surface disposed a distance away from the window. The space between the upper surface and the window may be filled by a fluid sample. In embodiments, such a cuvette may be centrifuged in an orientation in which the window is disposed farther from the center of rotation than the upper surface, effective that cells within the fluid sample are moved to a desired location (e.g., adjacent, or in contact with, the window). In embodiments, a chamber or channel configured for use with centrifugation in order to direct cells in a sample to a region near a window under the influence of such centrifugation, where such a region is suitable or optimal for imaging, may also include an adhesion agent on an inner surface of the chamber (e.g., on an optically transmissive surface of a window), such as a coating that binds cells to the window. Such a coating may comprise, for example, antibodies, nucleic acids, lectins, biotin, avidin, streptavidin, or other agents which may bind target analytes or cells. Thus, in embodiments, application of centrifugal force (e.g., due to centrifugation) may direct cells to a window, and may aid such immobilization as well.

Figure 5A:
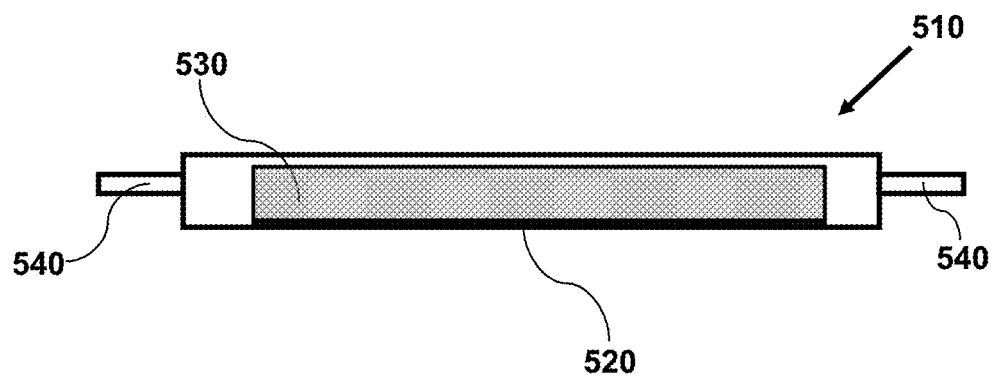
FIG. 5A provides a cross-sectional side view illustrating an imaging device with a sample within a channel, showing the channel and sample prior to centrifugation.
Figure 5B:
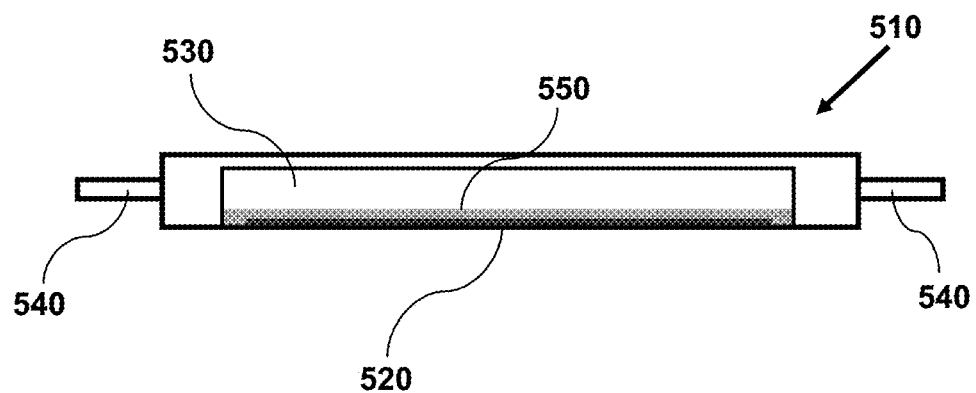
FIG. 5B provides a cross-sectional side view illustrating an imaging device with a sample within a channel, showing the channel and sample following centrifugation.

As shown in FIG. 5A, prior to centrifugation, cells are distributed throughout the chamber 530 of an imaging device 510 having a window 520 and having features as disclosed herein. Attachment elements 540 may be used to transport the device 510 to a centrifuge, and may be used to secure the device 510 during centrifugation. Following centrifugation, as illustrated in FIG. 5B by the area 550, most cells are disposed on the inner surface of window 520 within chamber 530 of an imaging device 510.

Methods for Imaging Cells in Microgravity Using Centrifugation

Applicant discloses methods in which cells in a fluid biological sample in microgravity conditions are subjected to centrifugation prior to enhance imaging of the cells in microgravity. Such centrifugation prior to imaging is effective to place cells in the fluid biological sample in a desired location for imaging. In embodiments, such a desired location is a location suitable for optimal imaging of the cells, e.g., a location on or adjacent to an optically transmissive surface such as a window.

Accordingly, a method of imaging cells in microgravity includes: placing a fluid biological sample in an imaging device having a sample chamber and a window (e.g., a wall, or portion of a wall, of the chamber that is optically transmissive); centrifuging the imaging device containing the fluid biological sample effective to move cells in the sample to a desired location within the imaging device; and imaging the cells. In embodiments, centrifugation is effective to move the cells to a location that is suitable, or that is optimal, for imaging the cells. In embodiments, the window comprises an optically transmissive surface, and may comprise adhesion agents; such adhesion agents may be effective to immobilize the cells on the window. In embodiments, centrifugation is effective to move the cells to a location that is adjacent to, or in contact with, the window. In embodiments, centrifugation is effective to move the cells so as to contact the window effective that adhesion agents coated on the window immobilize the cells on the window.

A further method of imaging cells in microgravity includes: providing an imaging device comprising a chamber having a window; introducing a sample into the chamber in microgravity; centrifuging the chamber containing the sample effective to move cells within the sample to the window; and imaging the cells. In embodiments, centrifugation is effective to move the cells to a location that is suitable, or that is optimal, for imaging the cells.

A further method of imaging cells in microgravity includes: providing an imaging device comprising a chamber having a window; introducing a sample into the chamber in microgravity; centrifuging the chamber containing the sample effective to move cells within the sample to the window; immobilizing the cells; and imaging the cells. In embodiments, centrifugation is effective to move the cells to a location that is suitable, or that is optimal, for imaging the cells. In embodiments, immobilizing the cells comprises contacting the cells with adhesion agents, where the adhesion agents are localized on an inner surface of the window. In embodiments, immobilizing the cells comprises providing a gel or matrix within the chamber containing the fluid biological sample, where providing said gel or matrix is performed following centrifugation and movement of the cells onto or adjacent the window.

In embodiments, centrifugation may be effective to provide centrifugal force to an imaging device (e.g., a cuvette), and to a fluid biological sample contained within an imaging device, of at least about 10×g, of at least about 100×g, of at least about 1000×g, of at least about 2000×g, of at least about 3000×g, of at least about 5000×g, of at least about 10,000×g, of at least about 20,000×g, or more. In embodiments, centrifugation may be performed for at least about 30 seconds, or for at least about one minute, or for at least about two minutes, or for at least about three minutes, or for at least about four minutes, or for at least about five minutes, or for at least about seven minutes, or for at least about nine minutes, or for at least about ten minutes, or for at least about fifteen minutes, or for at least about twenty minutes, or for at least about twenty five minutes, or for at least about thirty minutes, or for at least about forty minutes, or for at least about fifty minutes, or for at least about one hour, or for at least about ninety minutes, or for at least about two hours, or for at least about three hours, or more.

Accordingly, imaging of cells in a sample in microgravity may be aided by the use of centrifugation.

Systems for Imaging Cells Under Microgravity Conditions

Applicant discloses systems for imaging cells in a fluid biological sample in microgravity conditions. In embodiments of the systems disclosed herein, imaging devices in microgravity conditions, fluid biological samples in microgravity conditions, and cells within fluid biological samples in microgravity conditions are subjected to centrifugation prior to imaging to enhance imaging of the cells in microgravity. In embodiments of systems disclosed herein, a system includes an imaging device having a chamber for holding a fluid biological sample, and having an internal surface of the chamber that comprises an adhesion agent, wherein said adhesion agent is effective to immobilize cells within the chamber. In addition to, or in place of, an adhesion agent, an imaging device may comprise a gel or matrix for immobilizing cells within a fluid biological sample, as disclosed herein. In embodiments of systems disclosed herein, a system includes an imaging device having a chamber for holding a fluid biological sample, where the chamber includes magnetic particles. In embodiments of such systems comprising magnetic particles, the magnetic particles have targeting moieties which bind cells in the sample; such targeting moieties may include, for example, antibodies, nucleic acids, lectins, biotin, avidin, streptavidin, or other agents which may bind target analytes or cells. In embodiments of systems disclosed herein, a system includes an imaging device having a chamber for holding a fluid biological sample, where the chamber includes magnetic particles, and further includes a magnetic field source, e.g., a magnet. In embodiments, a magnetic field source may comprise an electromagnet. In embodiments of systems disclosed herein, a system includes an imaging device having a chamber for holding a fluid biological sample, where the chamber has a narrow portion configured to constrain cells within the biological sample to a location suitable for imaging; in embodiments, such a location suitable for imaging is adjacent to a window. In embodiments of systems disclosed herein, a system includes an imaging device having a chamber having at least two configurations, where one of the configurations comprises a chamber having a narrow portion configured to constrain cells within the biological sample to a location suitable for imaging; in embodiments, such a location suitable for imaging is adjacent to a window. In embodiments of systems disclosed herein, a system includes an imaging device having a chamber for holding a fluid biological sample as disclosed herein, and a centrifuge.

Accordingly, Applicant discloses herein a system for imaging cells from a fluid biological sample, comprising: a transportable device as disclosed herein; and an automatic sample analysis device comprising a fluid handling system configured to transport devices. In embodiments, the system further comprises a sample loading assembly. In embodiments, the system further comprises a communication assembly. In embodiments, the system further comprises an analysis assembly configured to perform two or more of general chemistry, nucleic acid, and immunochemistry analysis on said biological sample.

Accordingly, Applicant discloses herein a system for imaging cells from a fluid biological sample, comprising: a transportable device as disclosed herein; and an automatic sample analysis device comprising a fluid handling system configured to transport devices; and a magnetic field source. In embodiments, the system further comprises a sample loading assembly. In embodiments, the system further comprises a communication assembly. In embodiments, the system further comprises an analysis assembly configured to perform two or more of general chemistry, nucleic acid, and immunochemistry analysis on said biological sample.

Accordingly, Applicant discloses herein a system for imaging cells from a fluid biological sample, comprising: a transportable device as disclosed herein; and an automatic sample analysis device comprising a fluid handling system configured to transport devices; and a centrifuge. In embodiments, the system further comprises a sample loading assembly. In embodiments, the system further comprises a communication assembly. In embodiments, the system further comprises an analysis assembly configured to perform two or more of general chemistry, nucleic acid, and immunochemistry analysis on said biological sample.

Accordingly, Applicant discloses herein a system for imaging cells from a fluid biological sample, comprising: a transportable device as disclosed herein; and an automatic sample analysis device comprising a fluid handling system configured to transport devices; a magnetic field source; and a centrifuge. In embodiments, the system further comprises a sample loading assembly. In embodiments, the system further comprises a communication assembly. In embodiments, the system further comprises an analysis assembly configured to perform two or more of general chemistry, nucleic acid, and immunochemistry analysis on said biological sample.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, and so forth.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes:

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." As used in the description herein and throughout the claims that follow, the meaning of "in" includes "in" and "on" unless the context clearly dictates otherwise.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-2014 Theranos, Inc.

The invention claimed is:

1. A transportable device for imaging cells from a fluid biological sample, said transportable device comprising:
an optically transmissive external surface configured to transmit light from an illumination source;
a chamber comprising a window having an optically transmissive internal surface substantially parallel to said optically transmissive external surface; and
an entry port in fluid communication with said chamber and configured to receive a fluid biological sample comprising cells,
wherein said entry port and said chamber are configured to provide flow of fluid biological sample from said entry port across said optically transmissive internal surface, wherein said flow from the said entry port flows in a single direction directly over said window of said chamber, whereby said cells are positioned in a suitable position for imaging cells;
wherein said chamber comprises an adhesion coating placed on at least a majority portion of said window, wherein said adhesion coating is effective to bind cells from said biological sample to said optically transmissive internal surface, effective that cells within said fluid biological sample adhere to the optically transmissive internal surface for imaging,
wherein the chamber has a first chamber height and then a second, reduced chamber height downstream from a portion of the first chamber height;
wherein chamber height is measured from chamber ceiling to chamber floor;
wherein the chamber is of a cross-sectional size similar to a cross-sectional dimension of a cell from said fluid biological sample, wherein said chamber comprises a height of between about 15 micrometers (µm) and about 50 µm.

2. The device of claim 1, comprising a plurality of chambers, each of which chambers comprising a window having an optically transmissive internal surface and an entry port in fluid communication with said chamber and configured to receive a fluid biological sample comprising cells.

3. The device of claim 1, wherein said chamber comprises an elongated channel in fluid communication with said entry port.

4. The device of claim 1, said chamber comprising an outlet in fluid communication with said chamber.

5. The device of claim 4, wherein said outlet comprises a porous material, wherein said porous material is configured to allow fluid flow without allowing substantial loss of cells from said internal chamber.

6. The device of claim 1 comprising an adhesion coating placed on at least a portion of said window, wherein said adhesion coating is selected from the group consisting of: an antibody, an antibody fragment, an antibody mimic, an immunoadhesin, a cell receptor, a ligand, a nucleic acid, a nucleic acid analog, a polypeptide, a polymer, a lectin, a lipid, an oligosaccharide, a polysaccharide, biotin, avidin, a derivative thereof, and combinations thereof.

7. The device of claim 1, wherein said adhesion coating on said internal surface of said chamber comprises an antibody, an antibody fragment, an antibody mimic, or an immunoadhesin that specifically binds a target selected from the group consisting of: CD45, CD235, CD41, and CD61.

8. The device of claim 1, said chamber comprising a first section and a second section, wherein in a first configuration the chamber comprises a height that is greater than about 50 micrometers (µm), and in a second configuration the chamber comprises a height of between about 15 µm and about 50 µm.

9. The device of claim 1 wherein a first angled transition zone connects the first chamber to the second chamber.

10. The device of claim 1 wherein the chamber has the first chamber height then the second, reduced chamber height downstream, and then a third chamber height downstream from a portion with the reduced chamber height.

11. The device of claim 1 further comprising a second angled transition zone connects a portion of the chamber with the reduced chamber height to another portion with the third chamber height.

* * * * *